US007309611B2

(12) United States Patent
DiNello et al.

(10) Patent No.: US 7,309,611 B2
(45) Date of Patent: Dec. 18, 2007

(54) PREWETTING STOP FLOW TEST STRIP

(75) Inventors: Robert K. DiNello, Hayward, CA (US);
Alan J. Polito, Danville, CA (US);
Stella S. Quan, Moraga, CA (US)

(73) Assignee: Relia Diagnostic Systems, LLC, San Francisco, CA (US)

( * ) Notice: Subject to any disclaimer, the term of this patent is extended or adjusted under 35 U.S.C. 154(b) by 412 days.

(21) Appl. No.: 10/867,420

(22) Filed: Jun. 14, 2004

(65) Prior Publication Data
US 2004/0241882 A1 Dec. 2, 2004

Related U.S. Application Data

(62) Division of application No. 09/823,868, filed on Mar. 30, 2001, now Pat. No. 6,767,710.

(51) Int. Cl.
*G01N 33/53* (2006.01)
(52) U.S. Cl. .................. 436/514; 436/518; 436/164; 436/165; 436/169; 436/528; 436/530; 436/805; 436/807; 436/808; 436/810; 436/811; 436/817; 435/970; 435/810; 435/974; 435/975
(58) Field of Classification Search ................ 436/518, 436/164, 165, 169, 514, 528, 530, 805, 807, 436/808, 810, 811, 817; 435/970, 810, 974, 435/975
See application file for complete search history.

(56) References Cited

U.S. PATENT DOCUMENTS 4,703,017 A 10/1987 Campbell et al.
4,743,560 A 5/1988 Campbell et al.
4,943,522 A 7/1990 Eisinger et al.

(Continued)

FOREIGN PATENT DOCUMENTS

GB          2 204 398 A      11/1988
WO       WO 92/12428 A1      7/1992
WO          WO93/03176    *  2/1993

OTHER PUBLICATIONS

Bimbaum et al., "Latex-Based Thin-Layer Immunoaffinity Chromatography for Quantitation of Protein Analytes," *Analytical Biochem.* 206: 168-171 (1992).

(Continued)

*Primary Examiner*—Bao-Thuy L. Nguyen
(74) *Attorney, Agent, or Firm*—Cooley Godward Kronish LLP

(57) ABSTRACT

A test strip and method for detecting an analyte present in a sample. The test strip comprising: a buffer addition zone to which a buffer may be added; an absorbent zone proximal to the buffer addition zone; one or more test zones distal to the buffer addition zone, at least one of the test zones including a first analyte binding agent immobilized therein which is capable of binding to the analyte to be detected; a terminal buffer flow zone distal to the one or more test zones, the absorbent zone being positioned relative to the buffer addition zone and having an absorption capacity relative to the other zones of the test strip such that when a volume of buffer within a predetermined buffer volume range for the test strip is added to the buffer addition zone, a distal diffusion front of the buffer diffuses from the buffer addition zone to a distal diffusion point within the terminal buffer flow zone and then diffuses proximal relative to the one or more test zones; and a sample addition zone distal to the terminal buffer flow zone to which a sample may be added.

30 Claims, 17 Drawing Sheets

U.S. PATENT DOCUMENTS

| | | |
|---|---|---|
| 5,096,837 A | 3/1992 | Fan et al. |
| 5,232,835 A * | 8/1993 | Litman et al. ............. 435/7.93 |
| 5,238,652 A | 8/1993 | Sun et al. |
| 5,266,497 A | 11/1993 | Imai et al. |
| 5,660,993 A | 8/1997 | Cathey et al. |
| 5,726,010 A | 3/1998 | Clark |
| 5,750,333 A | 5/1998 | Clark |
| 5,753,517 A | 5/1998 | Brooks et al. |
| 6,007,999 A | 12/1999 | Clark |
| 6,136,610 A * | 10/2000 | Polito et al. ................ 436/514 |
| 6,284,194 B1 | 9/2001 | Chu |
| 6,528,323 B1 | 3/2003 | Thayer et al. |

OTHER PUBLICATIONS

Klimov et al., "Improved Immunochromatographic Format for Competitive-Type Assays," *Clinical Chem.* 41: 1360 (1995).

Roberts et al., "Investigation of Liposome-Based Immunomigration Sensors for the Detection of Polychlorinated Biphenyls," *Analytical Chem.* 67: 482-491 (1995).

* cited by examiner

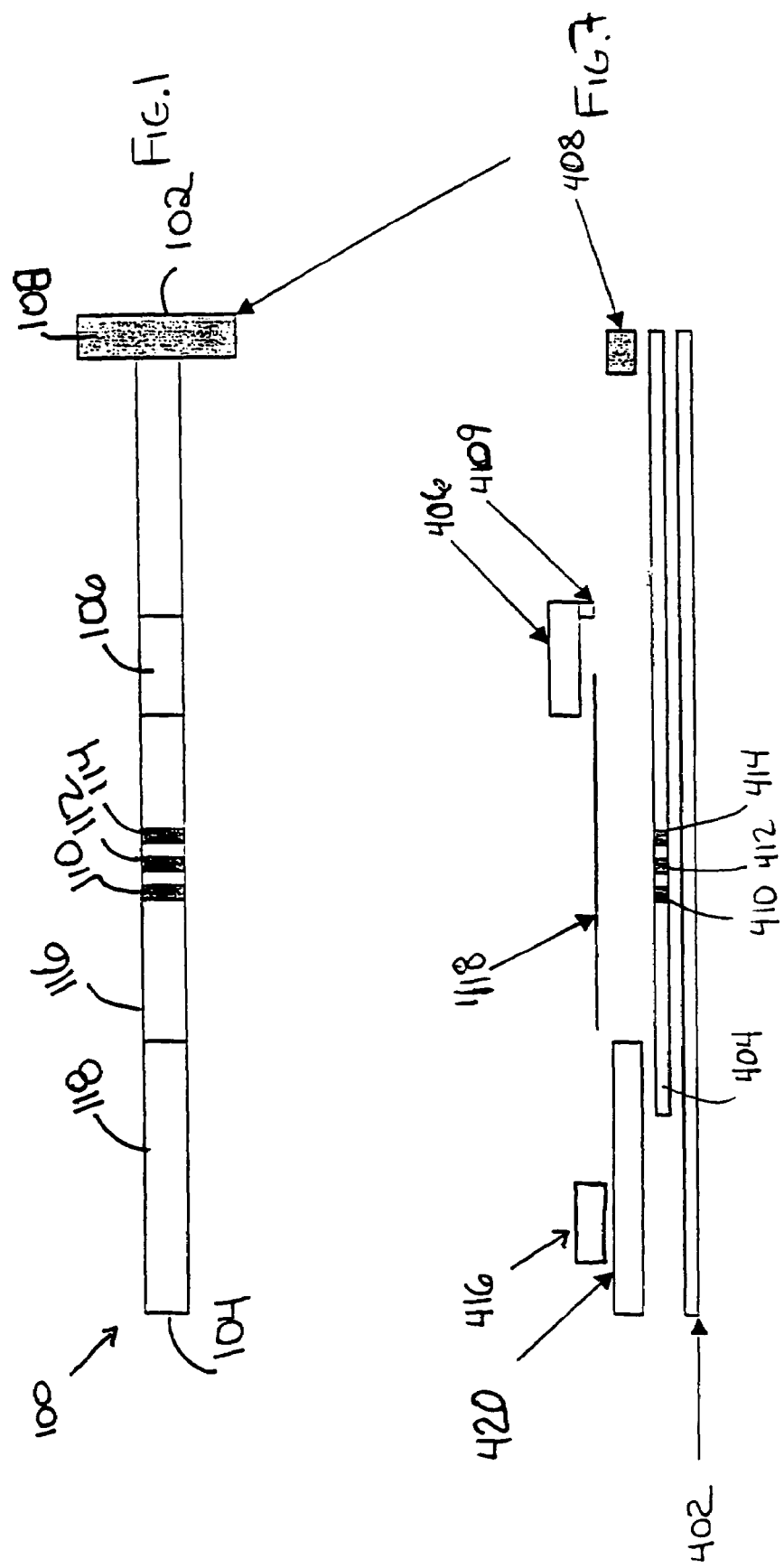

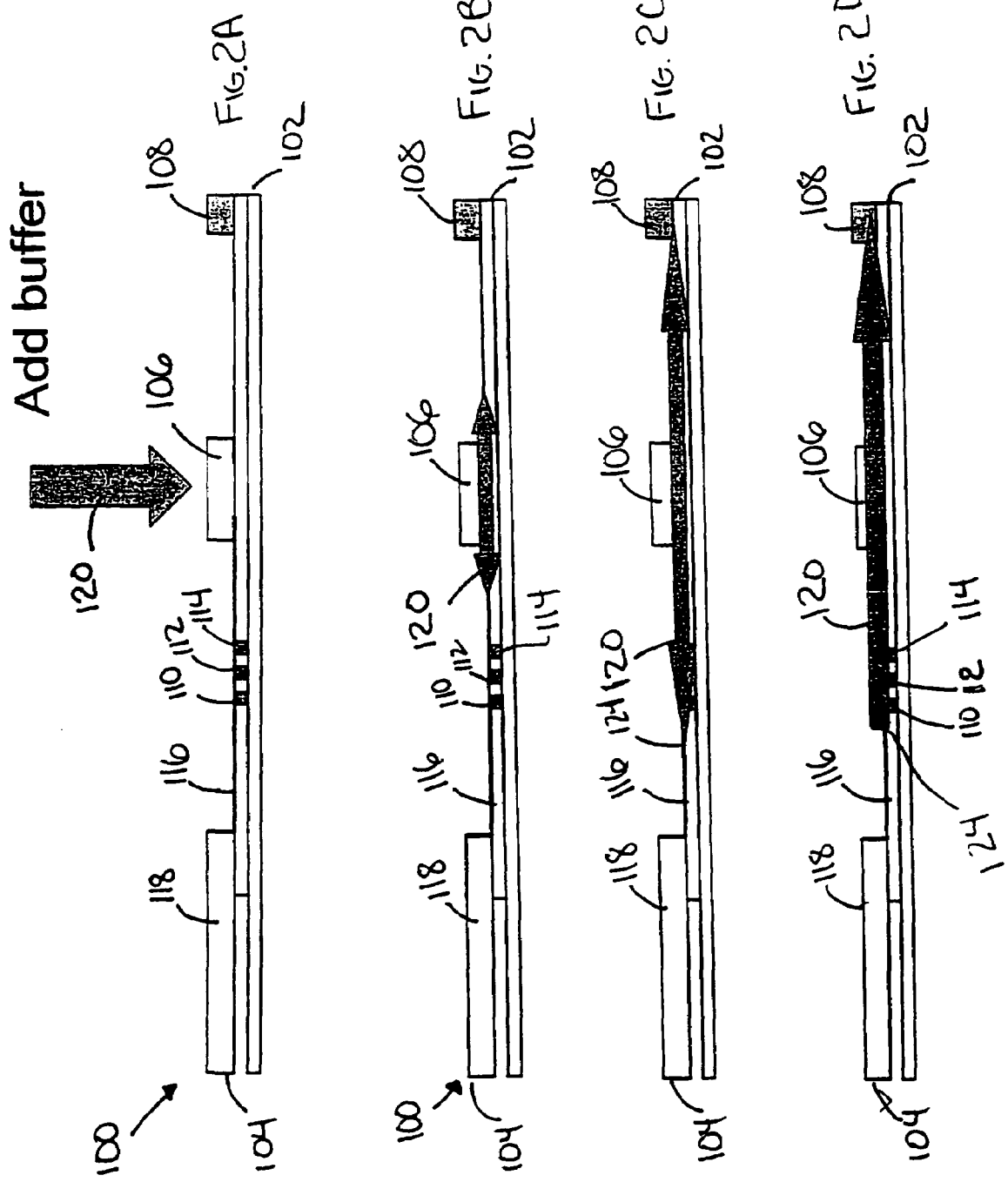

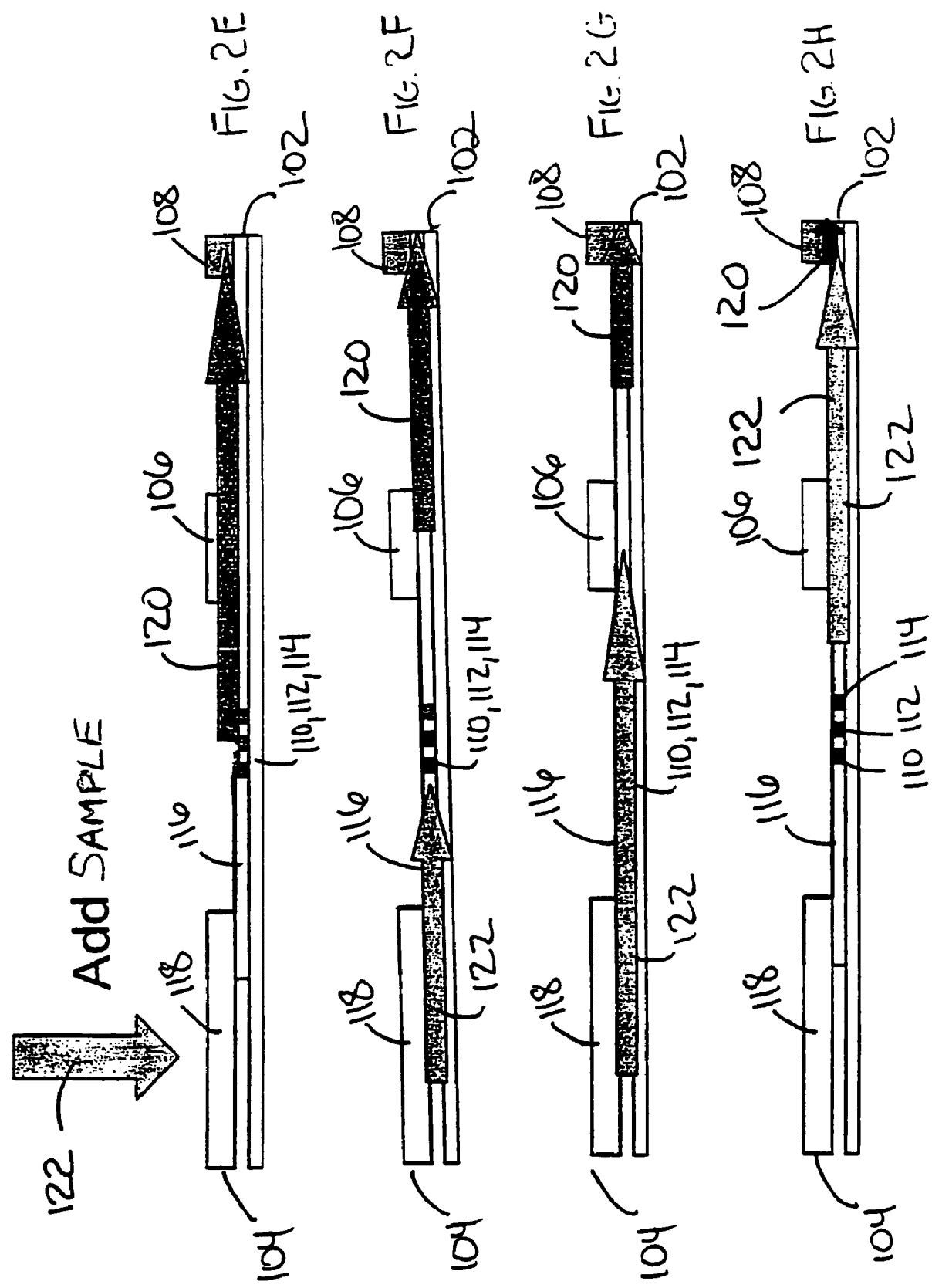

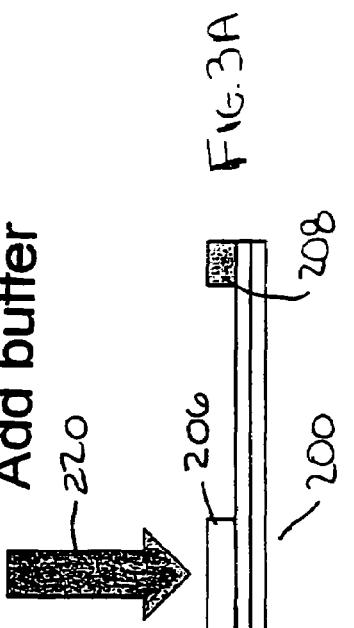
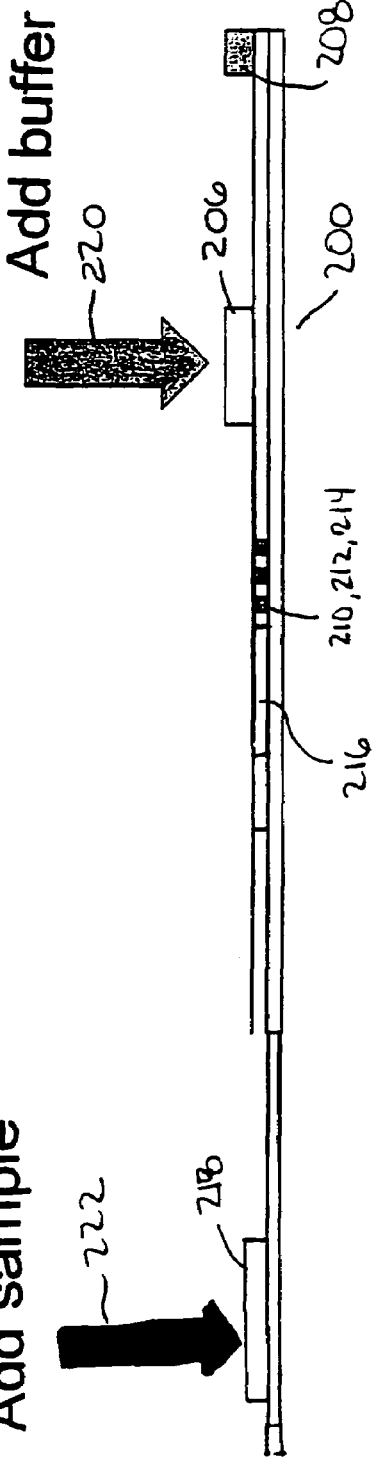
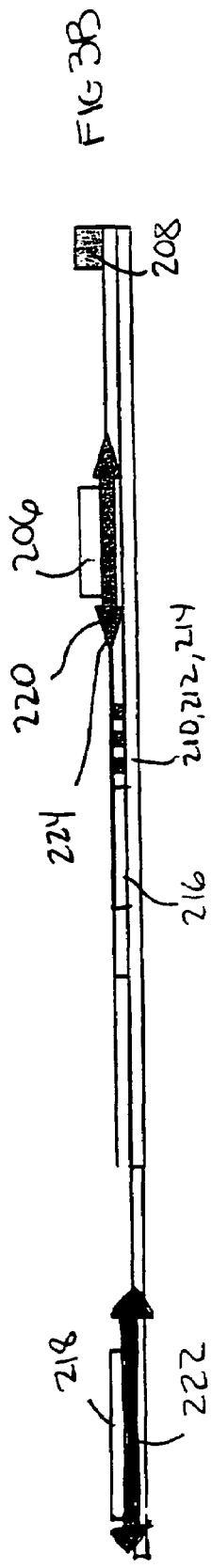
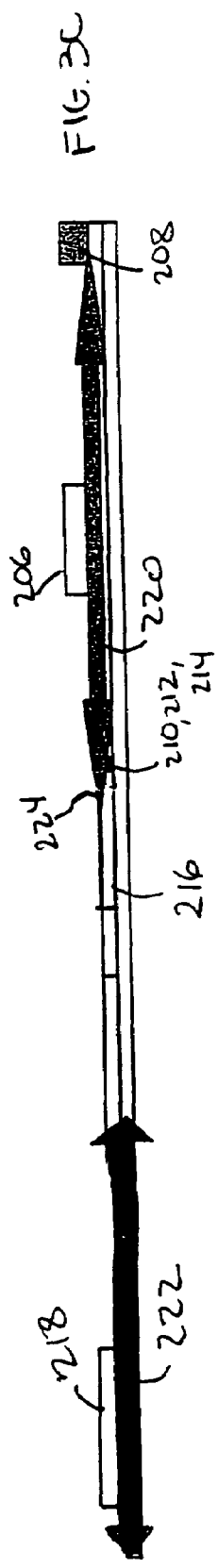
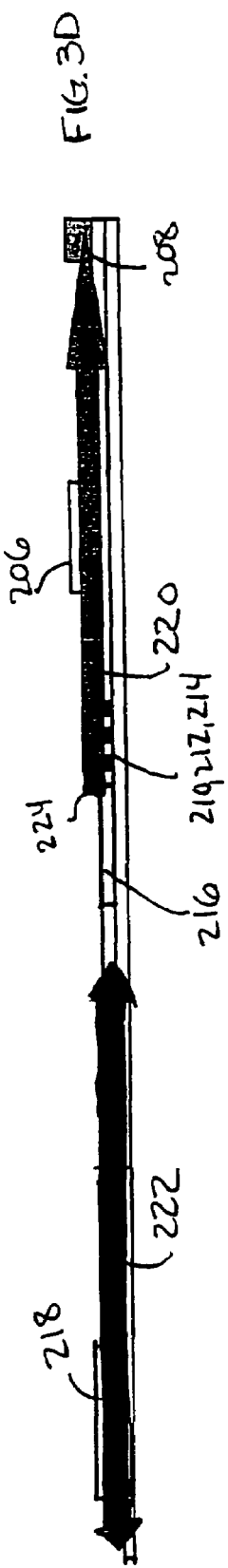

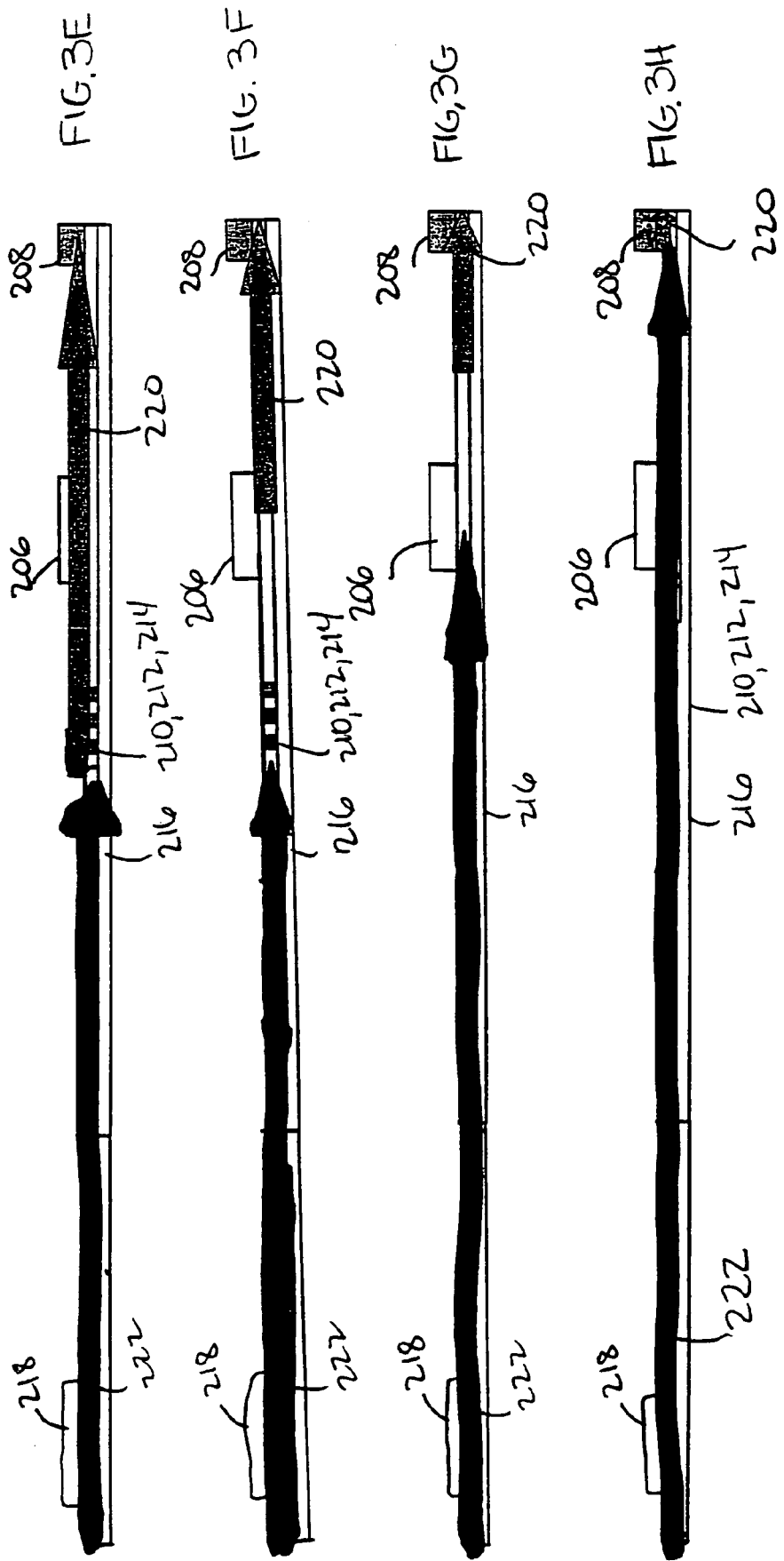

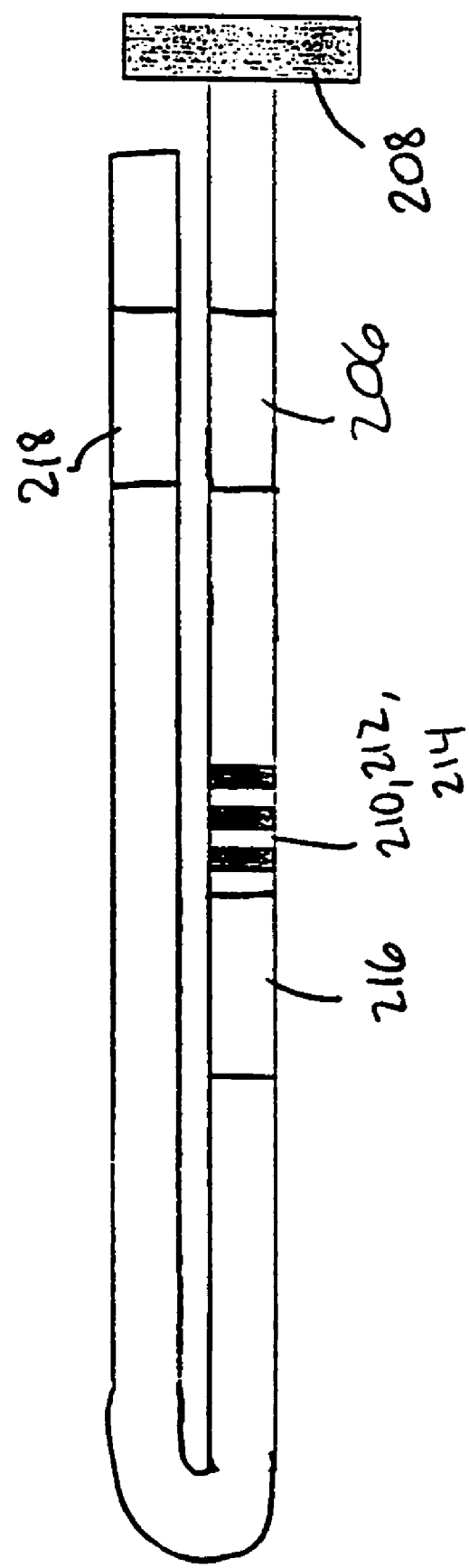

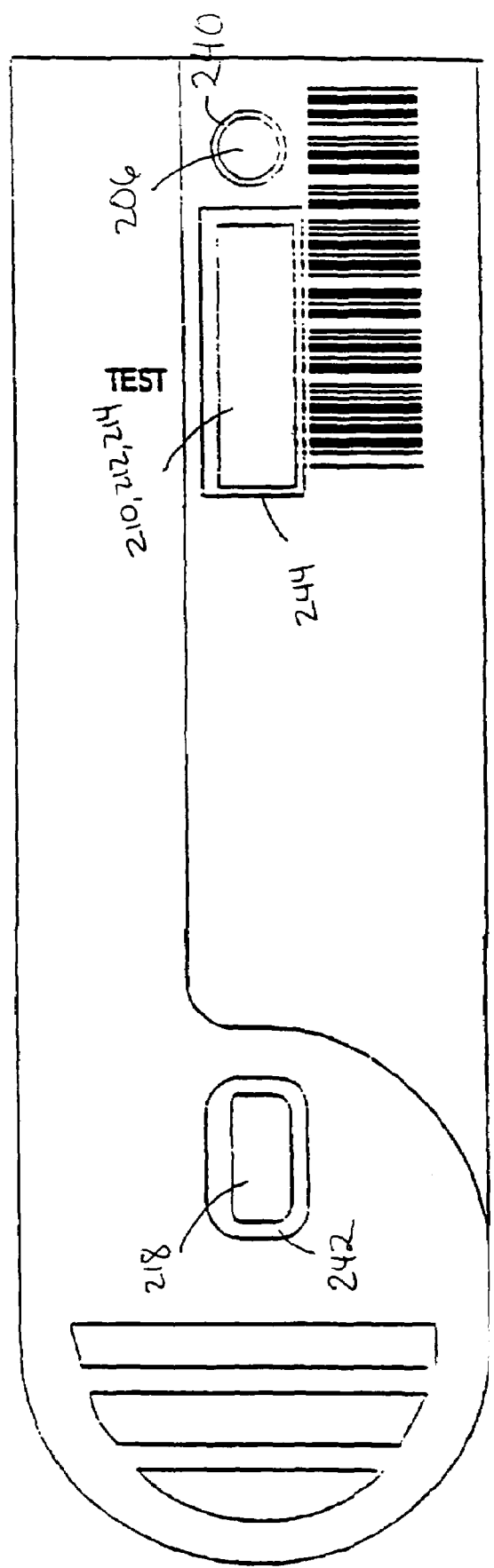

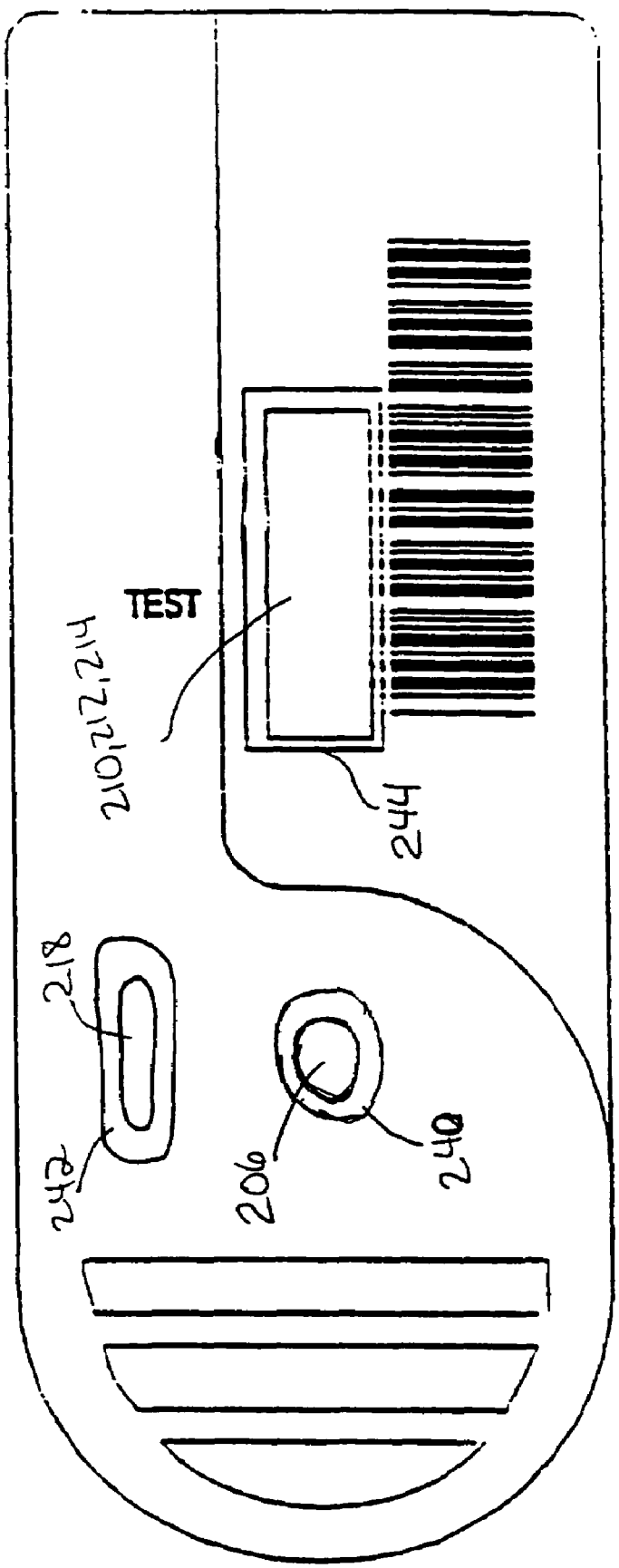

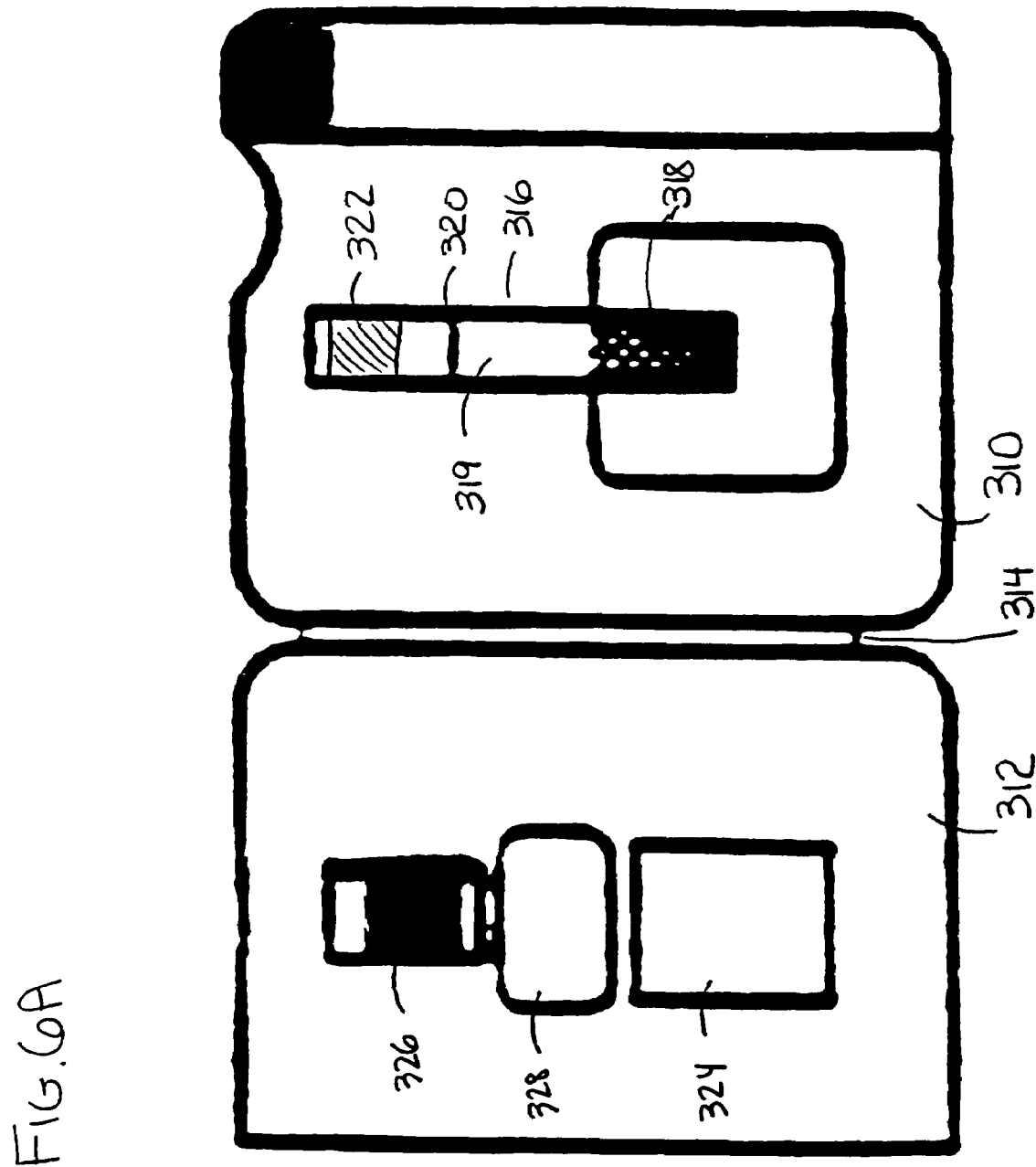

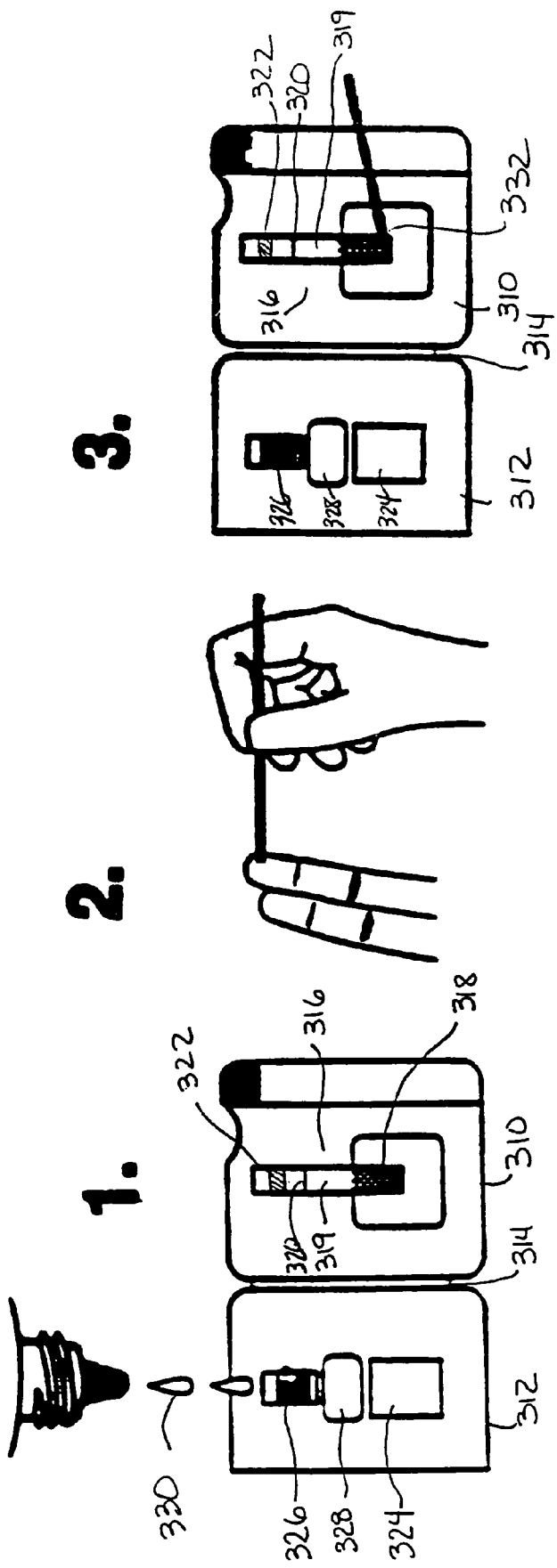

ReLIA™ TSH (Goat Capture)
160 µg/ml BSA-DNP in Release Buffer

FIGURE 8

| Sample | Sheet | Instrument | Hc (Dr) | Lc (Dr) | Specimen (Dr) | Hc/Lc | Specimen/HC | uIU/ml |
|---|---|---|---|---|---|---|---|---|
| 4A | 56R | 104 | 0.3229 | 0.2308 | 0.2153 | 1.399 | 0.6667 | 9.21 |
| 4A | 53R | 120 | 0.3306 | 0.2371 | 0.2073 | 1.394 | 0.6270 | 8.48 |
| 4A | 41R | 110 | 0.3002 | 0.2394 | 0.2010 | 1.254 | 0.6695 | 9.26 |
| 4A | 37R | 163 | 0.3252 | 0.2569 | 0.2112 | 1.266 | 0.6496 | 8.89 |
| 4A | 33R | 115 | 0.2941 | 0.2414 | 0.1942 | 1.218 | 0.6605 | 9.08 |
| 4A | 29R | 107 | 0.3031 | 0.2080 | 0.1980 | 1.457 | 0.6532 | 8.95 |
| 4A | 27R | 146 | 0.3375 | 0.2200 | 0.1980 | 1.534 | 0.5867 | 7.74 |
| 4A | 24R | 111 | 0.3136 | 0.2235 | 0.2010 | 1.403 | 0.6410 | 8.72 |
| 4A | 21R | 104 | 0.2995 | 0.2119 | 0.2024 | 1.413 | 0.6755 | 9.37 |
| 4A | 18R | 120 | 0.3213 | 0.2291 | 0.1959 | 1.403 | 0.6097 | 8.16 |
| 4A | 14R | 110 | 0.2902 | 0.2105 | 0.1917 | 1.378 | 0.6607 | 9.10 |
| 4A | 12R | 163 | 0.3176 | 0.2333 | 0.2128 | 1.361 | 0.6699 | 9.27 |
| 4A | 9R | 115 | 0.3156 | 0.2243 | 0.2050 | 1.407 | 0.6494 | 8.88 |
| 4A | 7R | 107 | 0.3170 | 0.2213 | 0.2140 | 1.432 | 0.6751 | 9.37 |
| 4A | 4R | 146 | 0.3367 | 0.2329 | 0.2110 | 1.446 | 0.6265 | 8.46 |
| 4A | 3R | 111 | 0.3409 | 0.2426 | 0.2237 | 1.405 | 0.6562 | 9.01 |
| AVG | | | 0.3166 | 0.2289 | 0.2052 | 1.3856 | 0.6486 | 8.87 |
| STD DEV | | | 0.0158 | 0.0132 | 0.0089 | 0.0799 | 0.0250 | 0.46 |
| %CV | | | 5.0 | 5.7 | 4.3 | 5.8 | 3.9 | 5.2 |

ReLIA™ PSA (Goat Capture)
160 μg/ml BSA-DNP in Release Buffer

FIGURE 10

| Sample | Sheet | Instrument | Hc (Dr) | Lc (Dr) | Specimen (Dr) | Hc/Lc | Specimen/HC | ng/ml |
|---|---|---|---|---|---|---|---|---|
| 2A | HF 135-24 | 163 | 0.2438 | 0.2469 | 0.1206 | 0.987 | 0.4948 | 9.70 |
| 2A | HF 135-23 | 165 | 0.2243 | 0.2252 | 0.0969 | 0.996 | 0.4318 | 8.20 |
| 2A | HF 135-20 | 104 | 0.2883 | 0.2543 | 0.1352 | 1.134 | 0.4690 | 9.07 |
| 2A | HF 135-21 | 120 | 0.2188 | 0.2165 | 0.0996 | 1.011 | 0.4553 | 8.75 |
| 2A | HF 135-31 | 115 | 0.2448 | 0.2113 | 0.1123 | 1.159 | 0.4586 | 8.83 |
| 2A | HF 135-30 | 107 | 0.2301 | 0.2283 | 0.1177 | 1.008 | 0.5117 | 10.11 |
| 2A | HF 135-27 | 111 | 0.2149 | 0.1825 | 0.1094 | 1.177 | 0.5089 | 10.05 |
| 2A | HF 135-25 | 146 | 0.2329 | 0.2206 | 0.1078 | 1.056 | 0.4629 | 8.93 |
| 2A | HF 135-36 | 163 | 0.2907 | 0.2558 | 0.1342 | 1.136 | 0.4617 | 8.90 |
| 2A | HF 135-35 | 165 | 0.3104 | 0.2988 | 0.1237 | 1.039 | 0.3984 | 7.45 |
| 2A | HF 135-33 | 104 | 0.2467 | 0.2507 | 0.1133 | 0.984 | 0.4595 | 8.85 |
| 2A | HF 135-34 | 120 | 0.2424 | 0.2270 | 0.1288 | 1.068 | 0.5313 | 10.62 |
| 2A | HF 135-18 | 115 | 0.2535 | 0.2529 | 0.1150 | 1.002 | 0.4535 | 8.71 |
| 2A | HF 135-37 | 107 | 0.2784 | 0.2633 | 0.1300 | 1.057 | 0.4672 | 9.02 |
| 2A | HF 135-19 | 111 | 0.2702 | 0.2701 | 0.1158 | 1.000 | 0.4288 | 8.14 |
| 2A | HF 135-29 | 146 | 0.2624 | 0.2314 | 0.1185 | 1.134 | 0.4515 | 8.66 |
| AVG | | | 0.2533 | 0.2397 | 0.1174 | 1.0593 | 0.4653 | 9.00 |
| STD DEV | | | 0.0279 | 0.0275 | 0.0112 | 0.0673 | 0.0334 | 0.80 |
| %CV | | | 11.0 | 11.5 | 9.5 | 6.4 | 7.2 | 8.9 |

FIGURE 12

Comparison of ReLIA TSH Assay With Sample Added to Top and Bottom Ports Versus Sample Added to Bottom Port Only

| Sample | | Sample Added to Top | | | | No Sample Added to Top | | | |
|---|---|---|---|---|---|---|---|---|---|
| | | HCDR | Specimen DR | Specimen DR / HCDR | TSH (uIU/mL) | HCDR | Specimen DR | Specimen DR / HCDR | TSH (uIU/mL) |
| S-25 Spiked | Mean | 0.2499 | 0.0243 | 0.0973 | 1.9068 | 0.204 | 0.0249 | 0.1262 | 2.4425 |
| | SD | 0.0154 | 0.017 | 0.0054 | 0.101 | 0.0359 | 0.007 | 0.0292 | 0.5276 |
| | CV | 6.2% | 7.0% | 5.5% | 5.3% | 17.6% | 2.9% | 23.1% | 21.6% |
| S-42 Spiked | Mean | 0.2566 | 0.0869 | 0.3399 | 6.2871 | 0.2219 | 0.0895 | 0.4056 | 7.4928 |
| | SD | 0.0199 | 0.0054 | 0.0275 | 0.4981 | 0.0249 | 0.0057 | 0.0281 | 0.5252 |
| | CV | 7.8% | 6.3% | 8.1% | 7.9% | 11.2% | 6.4% | 6.9% | 7.0% |
| Pool A | Mean | 0.2541 | 0.1369 | 0.5436 | 10.1692 | 0.2338 | 0.1394 | 0.6036 | 11.418 |
| | SD | 0.0312 | 0.0093 | 0.0497 | 1.0085 | 0.0362 | 0.0133 | 0.0675 | 1.4461 |
| | CV | 12.3% | 6.8% | 9.2% | 9.9% | 15.5% | 9.6% | 11.2% | 12.7% |
| Pool B | Mean | 0.2613 | 0.031 | 0.1186 | 2.308 | 0.2147 | 0.0289 | 0.1368 | 2.6254 |
| | SD | 0.0164 | 0.0021 | 0.0082 | 0.1526 | 0.0289 | 0.0025 | 0.0128 | 0.2336 |
| | CV | 6.3% | 6.8% | 6.9% | 6.6% | 13.4% | 8.7% | 9.4% | 8.9% |

Reproducibility of the ReLIA TSH Assay With Sample added to Top and Bottom

| TSH LEVEL | ReLIA Result in uIU/mL (N = 8 Replicates) | |
|---|---|---|
| Normal (Approx. 1 uIU/mL) | Mean | 1.0712 |
| | SD | 0.089 |
| | CV | 8.3% |
| Borderline Elevated (Approx. 5 uIU/mL) | Mean | 6.2425 |
| | SD | 0.551 |
| | CV | 8.8% |
| Elevated (Approx. 25 uIU/mL) | Mean | 23.631 |
| | SD | 1.658 |
| | CV | 7.0% |

PREWETTING STOP FLOW TEST STRIP

CROSS-REFERENCE TO RELATED APPLICATIONS

This application is a divisional of U.S. patent application Ser. No. 09/823,868, filed Mar. 30, 2001, now U.S. Pat. No. 6,767,710, from which application priority is claimed pursuant to 35 U.S.C. §120, and which application is incorporated herein by reference in its entirety.

BACKGROUND OF THE INVENTION

1. Field of the Invention

The present invention relates to lateral flow test strips and methods of operation for the lateral flow test strips.

2. Description of Related Art

Quantitative analysis of cells and analytes in fluid samples, particularly bodily fluid samples, often provides critical diagnostic and treatment information for physicians and patients. For example, immunological testing methods which take advantage of the high specificity of antigen-antibody reactions, provide one approach to measurement of analytes. Kennedy, D. M. and S. J. Challacombe, eds., ELISA and Other Solid Phase Immunoassays: Theoretical and Practical Aspects, John Wiley and Sons, Chichester (1988). This document and all others cited to herein, are incorporated by reference as if reproduced fully below. Such assays may also find use in various other applications, such as veterinary, food testing, or agricultural applications.

Immunoassays that provide a quantitative measurement of the amount of an analyte in a sample have previously used complex, multi-step procedures and expensive analyzers available only in a laboratory setting.

Immunochromatographic assays, such as those described in GB 2,204,398A; U.S. Pat. Nos. 5,096,837, 5,238,652, and 5,266,497; Birnbaum, S. et al., Analytical Biochem. 206: 168-171 (1992); Roberts, M. A. and R. A. Durst, Analytical Chem. 67:482-491 (1995); and Klimov, A. D. et al., Clinical Chem. 41:1360 (1995), are simpler, yet do not provide a quantitative measurement of an analyte. Instead, these immunochromatographic assays detect the presence (or absence) of an analyte above a defined cutoff level for the test performed. The lack of a quantitative measurement limits the usefulness of these assays.

A variety of disposable diagnostic assay devices have also been developed. Examples of such devices include, but are not limited to Cathey, et al, U.S. Pat. No. 5,660,993; International Publication Number WO 92/12428; Eisinger, et al, U.S. Pat. No. 4,943,522; ;Campbell, et al, U.S. Pat. No. 4,703,017; Campbell, et al, U.S. Pat. No. 4,743,560; and Brooks, U.S. Pat. No. 5,753,517. Nevertheless, a need still exists for improved disposable diagnostic assay devices and methods.

SUMMARY OF THE INVENTION

Test strips are provided which are adapted to receive a buffer that prewets the test strip and receive a sample which flows within the prewet test strip. The test strips are employed to detect one or more analytes that may be present in a sample.

According to one embodiment, the test strip comprises a buffer addition zone to which a buffer is added to prewet the test strip; an absorbent zone proximal to the buffer addition zone; one or more test zones distal to the buffer addition zone, at least one of the test zones including a first analyte binding agent immobilized therein which is capable of binding to the analyte to be detected; and a terminal buffer flow zone distal to the one or more test zones, the absorbent zone being positioned relative to the buffer addition zone and having an absorption capacity relative to the other zones of the test strip such that when a volume of buffer within a predetermined buffer volume range for the test strip is added to the buffer addition zone, a distal diffusion front of the buffer diffuses from the buffer addition zone to a distal diffusion point within the terminal buffer flow zone and then diffuses proximal relative to the one or more test zones. The test strip further comprises a sample addition zone that is distal to the terminal buffer flow zone. When a sample is added to the sample addition zone, the sample diffuses within the test strip in a proximal direction across the terminal buffer flow zone, across the one or more test zones, and ultimately to the absorbent zone. When the sample traverses the test zones, analyte in the sample is immobilized in whichever test zone(s) include(s) the first analyte binding agent bound therein.

The above described test strip may be used to detect an analyte in a sample by a direct detection assay or may be used to detect an analyte in a sample by a competitive assay. When the assay is a direct detection assay, the amount of analyte in the sample is measured based on the amount of analyte which is immobilized in a test zone by a first analyte binding agent bound therein. When the assay is a competitive assay, the test strip further comprises a competitive agent which is capable of competing with the analyte for binding to the first analyte binding agent. In this instance, the amount of analyte in the sample is measured based on how much less competitive agent is immobilized in the test zone by the first analyte binding agent as compared to when a control is employed as the sample which contains no analyte.

Control over the above described flow of the buffer within the test strip (i.e., such that the buffer reaches the terminal buffer flow zone and reverses the direction of buffer flow within the terminal buffer flow zone back toward the buffer addition zone and the absorbent zone) is achieved by controlling the amount of buffer added to the test strip within a predetermined range designed to be used with that test strip.

By adding the sample to the sample addition zone such that the sample reaches the terminal buffer flow zone after the buffer has reached the terminal buffer flow zone and has already reversed direction and is diffusing back toward the absorbent zone, the sample is able to flow within a prewet test strip, thereby yielding more accurate and precise results.

As will be described in greater detail herein, depending on the layout of the test strip, the buffer may be added before, at the same time, or after the sample is added to the test strip. For example, the sample addition zone may be positioned relative to the test zones such that sample is added to the sample addition zone at the same time that buffer is added to the buffer addition zone. The sample addition zone may also be positioned relative to the test zones such that sample added to the sample addition zone at the same time that the buffer is added to the buffer addition zone. The sample addition zone may also be positioned relative to the test zones such that the sample can be added to the test strip before the buffer is added and nevertheless, the sample still reaches the distal diffusion point of the buffer after the distal diffusion front of the buffer has diffused to the distal diffusion zone, reversed direction and begun diffusing in a proximal direction.

According to any of the above test strip embodiments, 1, 2, 3 or more test zones may be control zones with one or more control binding agents immobilized therein. The control zones may be used to calibrate the test strip, may be used to confirm whether or not the test strip performed as intended, may be used detect whether too little or too much buffer was added and may be used to detect whether too little sample was added.

In one embodiment, the test strip comprises at least a first control zone with a control binding agent immobilized therein. Optionally, the test zones further includes a second control zone with a same control binding agent immobilized therein as the first control zone. The first control zone may contain the same or a different amount of the control binding agent than the second control zone. In a preferred embodiment, the first control zone contains about the same amount of the control binding agent as the second control zone.

Also according to any of the above test strip embodiments, a second analyte binding agent which is capable of binding to the analyte and diffusing to the one or more test zones may be included on the test strip. The second analyte binding agent is preferably incorporated on the test strip adjacent either the sample addition zone or the buffer addition zone, more preferably proximal relative to the sample addition zone or distal relative to the buffer addition zone such that addition of the sample or buffer causes the second analyte binding agent to be carried with the sample or buffer to the test zones.

The second analyte binding agent may also be delivered to the test strip via the buffer or the sample, most preferably the sample. The second analyte binding agent may bind to components in the sample in addition to the analyte. Alternatively, the second analyte binding agent may be an agent which does not bind to components in the sample other than the analyte.

In order to facilitate detection, the second analyte binding agent is preferably labeled with a detectable marker. As discussed herein, any of a wide range of detectable markers known in the art may be used. In a preferred embodiment, the second analyte binding agent is attached to a particle which is capable of diffusing to the one or more test zones. The particle may serve as the detectable marker or may itself be labeled with a detectable marker.

Also according to any of the above test strip embodiments, the test strip may be for a competitive assay, in which case, the test strip may include a competitive agent. The competitive agent may compete with the analyte for binding to the first analyte binding agent.

The competitive agent is preferably incorporated on the test strip adjacent the sample addition zone, more preferably proximal relative to the sample addition zone such that addition of the sample causes the competitive agent to be carried with the sample to the test zone.

Methods are also provided for detecting an analyte in a sample.

In one embodiment, the method comprises delivering a buffer to a test strip which causes a distal diffusion front of the buffer to (a) diffuse in a distal direction to one or more test zones, at least one of the test zones including a first analyte binding agent immobilized therein which binds to analyte in the sample, (b) diffuse to a terminal buffer flow zone distal to the one or more test zones, change direction and (c) diffuse to a position proximal to the one or more test zones; delivering a sample to the test strip at a position distal to the terminal buffer flow zone, delivery of the sample causing analyte in the sample to diffuse proximally past the terminal buffer flow zone to the one or more test zones after the distal diffusion front of the buffer diffuses proximal to the one or more test zones, the analyte binding to the first analyte binding agent and becoming immobilized in the test zones; and detecting the analyte immobilized in the test zones.

According to the method, a second analyte binding agent may be present which binds to the analyte. The second analyte binding agent may be used to detect the immobilized analyte. The second analyte binding agent may be contained on the test strip where the sample is delivered, delivery of the sample causing the diffusion of the second analyte binding agent. Alternatively, the second analyte binding agent may be contained on the test strip proximal to where the sample is delivered, delivery of the sample causing the diffusion of the second analyte binding agent. Delivering the sample to the test strip may also include delivering the second analyte binding agent to the test strip within the sample.

In another embodiment, the method is for a competitive assay. According to this method, a buffer is delivered to a test strip which causes a distal diffusion front of the buffer to (a) diffuse in a distal direction to one or more test zones, at least one of the test zones including a first analyte binding agent immobilized therein which binds to analyte in the sample, (b) diffuse to a terminal buffer flow zone distal to the one or more test zones, change direction and (c) diffuse to a position proximal to the one or more test zones. A sample is also delivered to the test strip at a position distal to the terminal buffer flow zone such that delivery of the sample causes the sample diffuse proximally past the terminal buffer flow zone to the one or more test zones after the distal diffusion front of the buffer diffuses proximal to the one or more test zones.

Delivery of a sample to the test strip also causes a competitive agent to diffuse with the sample to the test zone. The competitive agent competes with the analyte for binding to the first analyte binding agent. The competitive agent is preferably incorporated on the test strip adjacent the sample addition zone, more preferably proximal relative to the sample addition zone such that addition of the sample causes the competitive agent to be carried with the sample to the test zone.

The method further comprises detecting the competitive agent immobilized in the test zones. In order to facilitate detection, the competitive agent is preferably labeled with a detectable marker.

According to any of the method embodiments, the buffer may be added to the test strip at a same time as the sample is added to the test strip, before the sample is added to the test strip, or after the sample is added to the test strip. When the sample is added to the test strip relative to the conjugate buffer depends on the time required for the buffer to reach the terminal buffer flow zone which, in turn, depends on the flow design of the test strip.

According to any of the above methods, the test zones may include a first control zone with a control binding agent immobilized therein, delivering the buffer causing a control agent to diffuse distally to the first control zone and bind to the control binding agent immobilized therein. Alternatively, the test zones may include first and second control zones which each include an approximately the same or significantly different amount of a control binding agent immobilized therein, delivering the buffer causing a control agent to diffuse distally to the first and second control zones and bind to the control binding agent immobilized therein.

When one or more control zones are employed, a control agent may be contained on the test strip where the buffer is delivered, delivery of the buffer causing the diffusion of the control agent. Alternatively, a control agent may be contained on the test strip distal to where the buffer is delivered, delivery of the buffer causing the diffusion of the control agent. Delivering the buffer to the test strip may also include delivering the control agent to the test strip -within the buffer. Incorporating the control agent into the buffer is advantageous because variability in the movement of control agents strip to strip arising from differences in the way in which the control agents becomes resolubilized when buffer is added is avoided.

Also according to the above methods, detecting the second analyte binding agent may be facilitated by labeling the second analyte binding agent with a detectable marker, detecting the second analyte binding agent including detecting the detectable marker. The second analyte binding agent may be attached to a particle. Detecting the second analyte binding agent may include detecting the particle.

According to any of the above embodiments, the buffer delivered to the test strip is preferably within a predetermined volume range that the test strip has been designed to process. The predetermined volume range is preferably between about 10 and 250 µL, preferably between about 20 and 200 µL, more preferably between about 20 and 100 µL, and most preferably between about 40 and 60 µL. When a buffer is delivered to the test strip within the predetermined volume range, the terminal buffer flow zone may be designed to have a short length from a proximal end to a distal end. For example, when a buffer is delivered to the test strip within a range of about 35 and 45 µL, the terminal flow zone may have a length from a proximal end to a distal end of between about 1 and 25 mm, more preferably 2 and 15 mm, and most preferably 3 and 10 mm.

Also according to any of the above embodiments, the first analyte binding agent preferably does not bind to components in the sample other than the analyte. Types of molecules that can serve as first analyte binding agents include, but are not limited to antibodies, engineered proteins, peptides, haptens, lysates containing heterogeneous mixtures of antigens having analyte binding sites, ligands and receptors. In one particular embodiment, the first analyte binding agent is an antibody or fragment thereof.

Also according to any of the above embodiments, the buffer added to the buffer addition zone may comprise the sample being tested. Optionally, the buffer may be the sample. When sample forms all or a portion of the buffer that is added to buffer addition zone, the buffer still performs the function of prewetting the test strip. The ability to use sample, in whole or in part, as the buffer allows the present invention to more easily accommodate a wider range of sample and external liquid control matrices (e.g., serum, plasma, euglobulin). In addition, differences in flow behavior within the test strip between sample and buffer can be reduced by adding the same composition (e.g., the sample) to both the sample and buffer addition zones.

BRIEF DESCRIPTION OF THE DRAWINGS

FIG. 1 illustrates a top-down view of an embodiment of a lateral flow test strip according to the present invention.

FIGS. 2A-2H illustrate a method of operation for a lateral flow test strip according to the present invention.

FIG. 2A illustrates a buffer being added to the test strip.

FIG. 2B illustrates the buffer flowing within the test strip.

FIG. 2C illustrates the test strip when the buffer has flowed a distance within the test strip in the direction opposite an absorbent zone to within a terminal buffer flow zone.

FIG. 2D illustrates the test strip where the buffer is flowing back toward the absorbent zone.

FIG. 2E illustrates the addition of a sample to the test strip.

FIG. 2F illustrates the flow of the sample within the test strip toward the absorbent zone.

FIG. 2G illustrates the flow of the sample within the test strip past the test zone.

FIG. 2H illustrates the flow of the sample within the test strip into the absorbent zone.

FIGS. 3A-3H a method of operation for a lateral flow test strip according to the present invention.

FIG. 3A illustrates a sample and buffer being added to the test strip.

FIG. 3B illustrates the sample and buffer flowing within the test strip.

FIG. 3C illustrates the test strip when the buffer has flowed a distance within the test strip in the direction opposite an absorbent zone to a to within terminal buffer flow zone.

FIG. 3D illustrates the test strip where the buffer is flowing back toward the absorbent zone.

FIG. 3E illustrates the sample continuing to flow toward the buffer flow.

FIG. 3F illustrates the sample having flowed past the terminal buffer flow zone.

FIG. 3G illustrates the flow of the sample within the test strip past the test zone.

FIG. 3H illustrates the flow of the sample within the test strip into the absorbent zone.

FIG. 4 illustrates a test strip design where the sample addition zone is positioned adjacent the buffer addition zone.

FIGS. 5A-5C illustrate various cartridge designs into which a test strip according to the present invention can be positioned.

FIG. 5A illustrates a cartridge design adapted for the test strip illustrated in FIGS. 2A-2H.

FIG. 5B illustrates a cartridge design adapted for the test strip illustrated in FIGS. 3A-3H where the buffer addition zone is positioned an extended distance from the sample addition zone such that the sample and wash buffer can be added at the same time.

FIG. 5C illustrates a cartridge design adapted for the test strip illustrated in FIG. 4 where the sample addition zone is positioned adjacent the buffer addition zone, the test zone being positioned an extended distance from the sample addition zone.

FIG. 6A illustrates the layout of a FLEXPACKJHP test strip manufactured by Abbott.

FIG. 6B illustrates the operation of the test strip illustrated in FIG. 6A.

FIG. 7 illustrates a side break-away view of the lateral flow test strip illustrated in FIG. 1.

FIG. 8 illustrates the results from the TSH assay performed in Example 2.

FIG. 10 illustrates the results from the PSA assay performed in Example 3.

FIG. 12 illustrates a comparison between the performance of the ReLIA™ TSH assay when sample is added to both the top and bottom ports and when sample is added only to the bottom port.

DESCRIPTION OF THE PREFERRED EMBODIMENTS

Figure 5A:
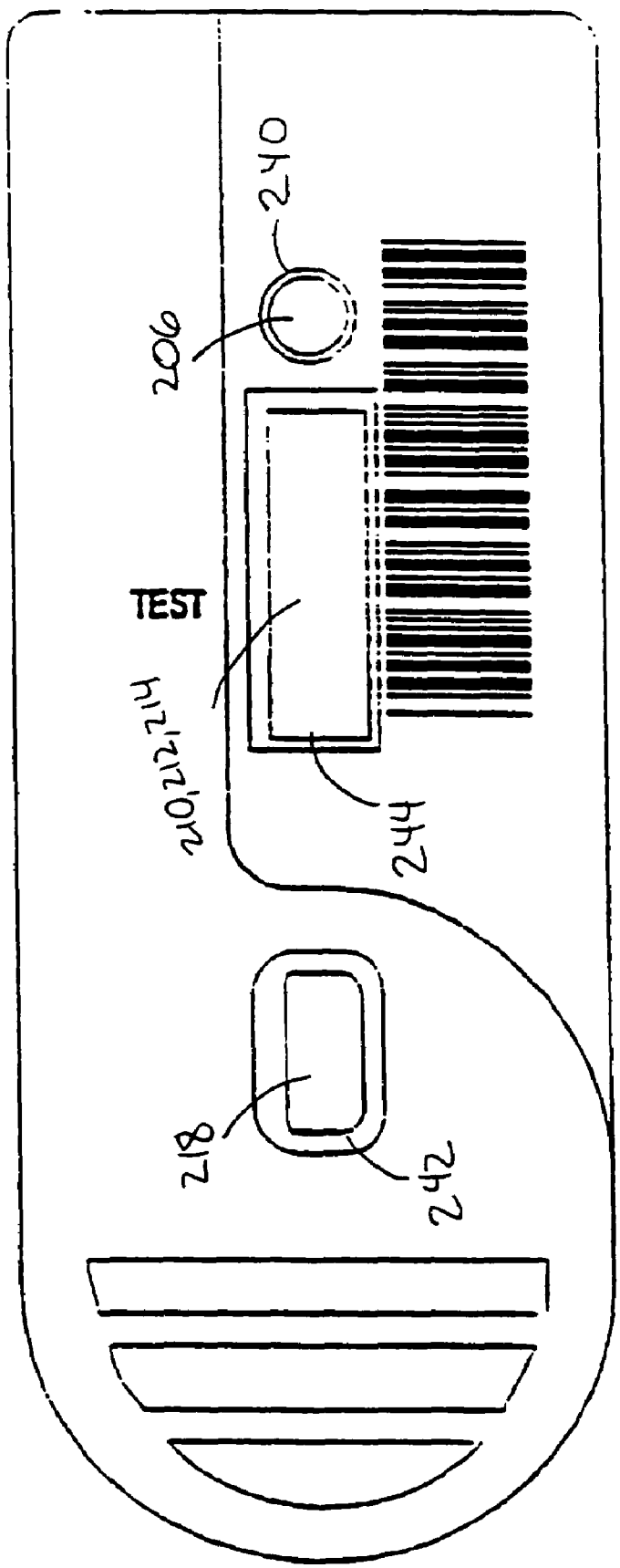

The present invention relates to lateral flow test strips and methods for employing such test strips which exhibit greater precision and accuracy. More specifically, the lateral flow test strips and methods of the present invention reduce performance variability, most likely due to interferences that might affect the absolute amount of binding of either analyte binding agent or control binding agent to a test zone, caused by variations in liquid flow rates across the test strip.

The present invention addresses the problem that the flow rate of a wet test strip is significantly different than the flow rate of a dry test strip. For example, fluid tends to flow faster when the test strip is dry than when it is wet. In order to minimize these flow rate influences, the present invention provides test strips which are designed to be prewet prior to the addition of a sample, thereby equilibrating the flow rate of the test strip so that a sample, once added, moves through the test strip at a more uniform rate across the test strip. In one embodiment, the test strip is prewet using the same sample that is being tested. By using the same sample as both a prewetting solution and as a sample, flow rate differences are further minimized.

Given that test strips need to yield reliable and consistent results independent of the person using the test strips, an important aspect of the present invention is the simplicity with which a test strip may be prewet to afford more uniform sample velocity. As will be discussed herein in greater detail, the design of the test strips of the present invention cause a prewetting solution, referred to herein as a buffer, to flow across the one or more test zones and control zones and then independently flow back toward the buffer addition zone without unintended portions of the strip becoming wet. This controlled flow and prewetting of the test strip accomplishes the desired results of providing a test strip that may be used with consistency, reproducibility and eliminates the need for operator intervention.

A further feature of the test strips of the present invention is the reduced timing sensitivity of the test strips regarding when buffer and sample is added to the test strip. Instead, the test strips of the present invention allow sample to be added within a broader time window after buffer is added.

Other factors influencing lateral flow test results include: 1) variability in the release of an analyte binding agent or the control agent from a conjugate pad, 2) device to device variation in the non-specific binding of the analyte binding population to the test strip, 3) variability in the movement of the analyte binding population through or along the test strip during the assay due to variation in the pore size of the test strip or membrane strip materials or non-specific aggregation of the analyte binding agent. These other sources of variability are also reduced by the test strips of the present invention.

According to one embodiment, a test strip is provided which comprises a buffer addition zone to which a buffer is added to prewet the test strip; an absorbent zone proximal to the buffer addition zone; one or more test zones distal to the buffer addition zone, at least one of the test zones including a first analyte binding agent immobilized therein which is capable of binding to the analyte to be detected; and a terminal buffer flow zone distal to the one or more test zones. The absorbent zone is positioned relative to the buffer addition zone and has an absorption capacity relative to the other zones of the test strip such that a distal diffusion front of a buffer added to the buffer addition zone diffuses from the buffer addition zone to a distal diffusion point within the terminal buffer flow zone and then reverses direction, independent of any user intervention, and diffuses proximal relative to the one or more test zones.

The independent flowing back of the buffer toward the buffer addition zone is achieved by positioning an absorbent zone relative to the buffer addition zone such that when a volume of buffer (within a predetermined volume range for that test strip) is added to the test strip, the diffusion front of the buffer expands across the one or more test zones to a terminal buffer flow zone. When the buffer reaches the terminal buffer flow zone, the absorbent properties of the absorbent zone causes the buffer to be drawn backward across the test zones toward the buffer addition zone and ultimately into the absorbent zone.

By causing buffer to flow across the one or more test zones and then independently flow back toward the buffer addition zone, the test strip is effectively prewet prior to the addition of sample. As a result, when sample is added to the test strip, the sample is believed to flow within the test strip at a more consistent velocity, thereby yielding more consistent results.

The ability to cause the buffer to flow back toward the buffer addition zone independent of any user interaction reduces the time criticality of when sample is added to the test strip. As will be discussed herein in greater detail, the self-timing features of test strips according to the present invention provides several significant advantages over previous test strips.

The test strip also comprises a sample addition zone that is distal to the terminal buffer flow zone. When a sample is added to the sample addition zone, the sample diffuses within the test strip in a proximal direction across the terminal buffer flow zone, across the one or more test zones, and ultimately to the absorbent zone. Analyte in the sample binds to one or more test zones and is detected there.

FIG. 1 illustrates a top-down view of an embodiment of a lateral flow test strip 100 according to the present invention. As illustrated, the test strip 100 has proximal and distal ends 102, 104 respectively and can be divided into several different zones. The test strip includes a buffer addition zone 106 where a buffer may be added to the test strip 100. An absorbent zone 108 is positioned proximal to the buffer addition zone 106. One or more test zones 110, 112, 114 are positioned distal to the buffer addition zone 106. The test strip 100 also includes a terminal buffer flow zone 116 distal to the one or more test zones 110, 112, 114. Each of the above mentioned zones are in fluid diffusion communication with each other.

As illustrated, the test strip also includes a sample addition zone 118 distal to the terminal buffer flow zone 116. The sample addition zone 118 may be a zone where sample may be added to the test strip. Alternatively, the sample addition zone 118 may simply correspond to a zone to which sample diffuses from a more distal point on the test strip.

The test strip may also include a zone distal to the terminal buffer flow zone 116 which includes either a second analyte binding agent in the case of a direct assay or a competitive agent in the case of a competitive assay. In FIG. 1, the sample addition zone 118 may serve as the zone comprising the second analyte binding agent or the competitive agent. Alternatively, the zone comprising the second analyte binding agent or the competitive agent may be proximal to the sample addition zone 118.

It is noted that the layout of the test strip illustrated in FIG. 1 is linear in design. However, non-linear layouts, such as the layout illustrated in FIG. 4, are also intended for the test strips according to the present invention.

FIGS. 2A-2H illustrate a method of operation of a lateral flow test strip, such as the one illustrated in FIG. 1. Prior to performing an assay using a test strip according to the present invention, a fluid sample is obtained that is believed to contain the analyte to be detected. The sample can include any fluid that wets the test strip and has a viscosity that is sufficient to allow movement of the sample across the test strip. In a preferred embodiment, the sample is an aqueous solution (such as a bodily fluid).

Also prior to performing an assay, buffer is obtained which is to be added to the test strip. As described herein, the buffer may optionally contain a control agent. Incorporating the control agent into the buffer is advantageous because variability in the movement of control agents strip to strip arising from differences in the way in which the control agents becomes resolubilized when buffer is added is avoided. As also described herein, the buffer added to the buffer addition zone may comprise the sample being tested. Optionally, the buffer may be the sample. When sample forms all or a portion of the buffer that is added to buffer addition zone, the buffer still performs the function of prewetting the test strip. The ability to use sample, in whole or in part, as the buffer allows the present invention to more easily accommodate a wider range of sample and external liquid control matrices (serum, plasma, euglobulin). In addition, differences in flow behavior within the test strip between sample and buffer can be reduced by adding the same composition (e.g., the sample) to both the sample and buffer addition zones.

FIG. 2A illustrates buffer 120 being added to the buffer addition zone 106 of the test strip 100. It is noted that the test strip is designed for use with a volume of buffer that is within a particular volume range. More specifically, delivering buffer to the buffer addition zone within the predetermined volume range causes the buffer to diffuse distally beyond the test zones into the terminal buffer flow zone 116, but not beyond the terminal buffer flow zone 116 (as illustrated in FIG. 2D).

As illustrated in FIG. 2B, the buffer 120 begins to diffuse both proximally and distally across the test strip after being added to the test strip. As illustrated in FIG. 2C, the distal front 124 of the buffer 120 diffuses across the one or more test zones 110, 112, 114 to within the terminal buffer flow zone 116. As illustrated in FIG. 2D, the distal front 124 of the buffer 120 ultimately extends to a point within the terminal buffer flow zone 116.

When the volume of the buffer added to the test strip is within a predetermined volume range for which the test strip is designed, the distal front 124 of the buffer 120 reaches a distal diffusion point corresponding to a point of maximum distal flow somewhere within the terminal buffer flow zone 116. At this point, as illustrated in FIG. 2E, capillary action by the absorbent zone 108 draws the buffer proximally toward the absorbent zone 108. As the buffer is drawn into the absorbent zone 108, the distal front 124 of the buffer recedes proximally.

As can be seen from FIGS. 2A-2D, a feature of the present invention is the control of where and how the buffer flows within the test strip. The buffer delivered to the test strip is preferably within a predetermined volume range that the test strip has been designed to process. The predetermined volume range is preferably between about 10 and 250 µL, preferably between about 20 and 200 µL, more preferably between about 20 and 100 µL, and most preferably between about 40 and 60 µL. When buffer is delivered to a test strip within these ranges, the flow of the buffer stops within the terminal buffer flow zone.

The terminal buffer flow zone may be designed to have a short length from a proximal end to a distal end. For example, when buffer is delivered to the test strip within a range of about 35 and 45 µL, the terminal buffer flow zone may have a length from a proximal end to a distal end of between about 1 and 25 mm, more preferably 2 and 15 mm, and most preferably 3 and 10 mm.

Positioned within one of the test zones (e.g., test zone 112) is a first analyte binding agent which binds to an analyte in a sample which the test strip is designed to detect. Analyte present in the portion of the sample which flows across the test zones is immobilized in test zone 112 by the first analyte binding agent.

FIG. 2E illustrates the addition of a sample 122 to the test strip at the sample addition zone 118 after the buffer has reached the terminal buffer flow zone. The volume of sample added is preferably between about 10 and 250 µL, preferably between about 20 and 150 µL, more preferably between about 50 and 150 µL, and most preferably between about 75 and 125 µL. It is noted that the most preferred volume of sample to add to a test strip will vary depending on the assay.

The sample 122 may contain one or more different second analyte binding agents which can bind to the analyte and enable analyte immobilized in the test zones to be detected. It is noted that the sample addition zone 118 may optionally include the one or more second analyte binding agents used to detect immobilized analyte. In that instance, addition of the sample 122 serves to initiate diffusion of the one or more second analyte binding agents across the test zones.

As illustrated in FIGS. 2F and 2G, the sample 122 flows proximally across the test strip toward the absorbent zone 108, thereby causing both analytes in the sample and the one or more second analyte binding agents to move across the test zones 110, 112, 114 and bind to immobilized analyte.

As illustrated in FIG. 2H, capillary action by the absorbent zone 108 causes the buffer 120 to diffuse into the absorbent zone 108. Meanwhile, the sample 122 continues to diffuse proximally across the test zones 110, 112, 114 and into the absorbent zone 108. Any of the one or more second analyte binding agents that were not immobilized in the test zones 110, 112, 114 are carried with the sample 122 into the absorbent zone 108.

In regard to the embodiment illustrated in FIGS. 2A-2H, it is noted that the sample 122 should be added to the test strip after the buffer 120 has reached the test zones 110, 112, 114 and preferably after the buffer has reached the terminal buffer flow zone 116 and has begun to diffuse back toward the absorbent zone 108. This allows the buffer 120 to prewet the test strip.

FIGS. 3A-3H illustrate an alternative test strip design and method of operation for the test strip. In this embodiment, the buffer and sample are added at the same time. In order for the buffer and sample to be added at about the same time, it is necessary for the sample to reach the test zones 210, 212, 214 after the buffer has contacted the test zones. It is preferred that the sample reach the test zones after the buffer has begun diffusing back across the test zones toward the absorbent zone 208.

Delaying when the sample reaches the test zones is accomplished in this embodiment by creating a longer distance between sample addition zone 218 and the terminal buffer flow zone 216 as compared to the test strip design illustrated in FIGS. 2A-2H. Alternatively, one can use a material which causes the sample to diffuse at a slower rate.

FIG. 3A illustrates a buffer 220 being added to a buffer addition zone 206 of the test strip 200. Meanwhile, a sample 222 is added to a sample addition zone 218 at about the same time that the buffer is added to the test strip.

As illustrated in FIG. 3B, the buffer 220 begins to diffuse both proximally and distally within the test strip once added to the test strip. Meanwhile, the sample 222 also diffuses proximally and optionally distally within the test strip.

As illustrated in FIG. 3C, the distal front 224 of the buffer 220 diffuses across one or more test zones 210, 212, 214 to within a terminal buffer flow zone 216. Meanwhile, the sample 222 continues to diffuse proximally within the test strip toward the test zones.

As illustrated in FIG. 3D, the distal front 224 of the buffer 220 ultimately extends to a point within the terminal buffer flow zone 216. At the time when the buffer is in the terminal buffer flow zone 216, the sample 222 has not yet reached that zone.

As illustrated in FIG. 3E, capillary action by the absorbent zone 208 draws the buffer proximally toward the absorbent zone 208. As the buffer is drawn into the absorbent zone 208, the distal front 224 of the buffer flows proximally.

FIG. 3F illustrates the sample 222 reaching the test zones. As can be seen, by the time the sample 222 reaches the test zones, the distal front 224 of the buffer has already flowed proximally out of the terminal buffer flow zone 216 and the test zones 210, 212, 214. Positioned within one of the test zones (e.g., test zone 212) is a first analyte binding agent which binds to analyte in the sample which the test strip is designed to detect. Analyte present in the portion of the sample which flows across the test zones is immobilized in test zone 212 by the first analyte binding agent.

As illustrated in FIGS. 3G and 3H, capillary action by the absorbent zone 208 causes the buffer to withdraw into the absorbent zone 208. Meanwhile, the sample 222 continues to diffuse proximally across the test zones 210, 212, 214 and into the absorbent zone 208. Any of the one or more second analyte binding agents that were not immobilized in the test zones 210, 212, 214 are carried with the sample 222 into the absorbent zone 208.

The sample 222 added to the test strip may contain one or more second analyte binding agents which can bind to the analyte and enable analyte immobilized in the test zones to be detected. Alternatively, the test strip may include a conjugate zone distal to the terminal buffer flow zone 216 which contains one or more second analyte binding agents. The sample addition zone 218 may also serve as the conjugate zone. When the one or more second analyte binding agents are preloaded onto the test strip, the sample 222 serves to initiate diffusion of the one or more second analyte binding agents across the test zones toward the absorbent zone.

As illustrated in FIGS. 3A-3H, the sample may be added to the test strip before the buffer reaches the test zones by designing the diffusion path of the test strip such that the sample does not reach the test zones until after the buffer has diffused over and then back from the test zones. It is noted that the diffusion of the sample to the test zones may be sufficiently delayed that one adds the sample to the test strip prior to adding the buffer to the test strip.

In regard to the embodiments illustrated in FIGS. 2A-2H and 3A-3H, it is noted that the method is a direct assay, i.e., the amount of analyte present is measured by measuring the amount of analyte immobilized in a test zone. Competitive assays, i.e., assays where the amount of analyte present is measured by measuring how much less of a competitive agent is immobilized in a test zone. In order to perform a competitive assay, the operation of the test strips illustrated in FIGS. 2A-2H and 3A-3H need only be modified by employing a competitive agent which competes with the analyte to bind to the first analyte binding agent.

FIG. 4 illustrates an alternative test strip design for a lateral flow test strip according to the present invention. The operation of the test strip is similar to the operation described in FIGS. 3A-3H. The same reference numerals are employed in FIG. 4 as in FIGS. 3A-3H. As illustrated in FIG. 4, the buffer addition zone 206 is positioned adjacent the sample addition zone 218. This allows for a more compact test strip design while also allowing the sample and buffer to be added simultaneously.

One feature of the test strip design illustrated in FIG. 4 is that the sample and buffer are added to the same end of the test strip. It is also noted that the test zones 210, 212, 214 are positioned toward an opposite end of the sample and buffer addition zones 206, 218. This makes it possible for the test zones to be positioned within a sample reader while the sample and buffer addition zones are outside the sample reader. This, in turn, allows sample and buffer to be added to the test strip while the test strip is in a test strip reader.

FIGS. 5A-5C illustrate various cartridge designs into which test strips according to the present invention can be positioned. In each cartridge design, the cartridge includes a buffer addition port 240 adjacent the buffer addition zone 206 of the test strip. The cartridge also includes a sample addition port 242 adjacent the sample addition zone 218 of the test strip. The cartridge also includes a test window 244 adjacent the test zones 210, 212, 214 of the test strip.

FIG. 5A illustrates a cartridge design adapted for the test strip illustrated in FIGS. 2A-2H. FIG. 5B illustrates a cartridge design adapted for the test strip illustrated in FIGS. 3A-3H where the buffer addition zone is positioned an extended distance from the sample addition zone such that the sample and buffer can be added to the test strip at about the same time. FIG. 5C illustrates a cartridge design adapted for the test strip illustrated in FIG. 4 where the buffer addition zone is positioned adjacent the sample addition zone, the test zone being positioned an extended distance from the sample addition zone.

It is noted with regard to FIGS. 2-4 that a feature of the test strips of the present invention is the test strip's inherent ability to expose test zones on the test strip to buffer for a period of time and then to cause the buffer to diffuse away from the test zones prior to the sample reaching the test zones. This feature is made possible by matching (1) the positioning of the absorbent zone relative to the buffer addition zone with (2) the absorbent capacity of the test strip between the buffer addition zone and the terminal buffer flow zone and (3) the volume of the buffer to be delivered to the test strip. If too much buffer is delivered, the buffer will diffuse beyond the terminal buffer flow zone. If too little buffer is delivered, the buffer does not diffuse far enough in the test strip to reach the test zones and thus does not adequately prewet the test strip.

The test strip's ability to expose the test zones to buffer for a limited period of time and then cause the buffer to be removed from the test zones confers a timing independence to the test strip which enhances the test strip's precision and ease of use. For example, test results are not dependent on when the sample and buffer are added to the test strip. As a result, the test strips need not be carefully monitored regarding when the sample should be added. In this regard, the window of time after the buffer has been added when sample should be added to the test strip is substantially eliminated by the present invention.

The dynamics of using the volume of the buffer delivered to the test strip to control how the buffer diffuses within the test strip will now be illustrated in regard to FIG. 1. As discussed previously, FIG. 1 illustrates a test strip which has proximal and distal ends 102, 104 respectively and is divided into several distinct zones. The test strip includes a buffer addition zone 106 where a buffer is added to the test strip. An absorbent zone 108 is positioned proximal to the buffer addition zone 106. A test zone 112 is positioned distal to the buffer addition zone 106. A terminal buffer flow zone 116 is positioned distal to the test zone 112. A sample addition zone 118 is positioned distal to the terminal buffer flow zone 116.

For the purpose of illustration, assume that the test zone 112 includes a first analyte binding agent and the sample addition zone 118 includes a second analyte binding agent labeled with a detectable marker. Also assume that the test strip is designed such that a buffer volume of 30 µL will cause the buffer to diffuse to but not beyond the test zone 112. Meanwhile, a buffer volume of 50 µL will cause the buffer to diffuse to the distal end of the terminal buffer flow zone 116.

If buffer is delivered to the test strip within the 30-50 µL volume range, the distal front of the buffer will diffuse past the test zone 112. Distal advancement of the buffer will stop within the terminal buffer flow zone 116. The buffer then flows back in the proximal direction toward the absorbent zone 108 past the test zone 112, thereby prewetting the test strip. When the sample is added, the sample causes the analyte in the sample and the second analyte binding agent to diffuse across the test zone 112. The second analyte binding agent binds to the analyte which in turn binds to the first analyte binding agent immobilized in the test zone 112. Other components in the sample will not bind to the first analyte binding agent antibody since the first analyte binding agent is selective for the analyte. Since the buffer diffuses away from the test zone 112 prior to the sample reaching the test zone 112, the prior addition of the buffer prewets the test strip but the flow of the buffer does not interfere with the flow of the sample within the test strip.

If a buffer volume of less than 30 µL is delivered (e.g., 25 µL) to the test strip, the buffer never diffuses to the test zone 112. As a result, the buffer does not prewet the test strip in the test zone 112. When the sample is added, the sample has to flow across a combination of dry test strip and wet test strip which can create variations due to differences in flow rates.

If the buffer volume delivered is greater than 50 µL (e.g., 55 µL), the buffer will diffuse past the test zone 112 and past the terminal buffer flow zone 116 into the sample addition zone. When too much buffer is added, the test strip could be flooded, thereby interfering with the test strip's operation. Also, in some embodiments, the buffer could cause diffusion of a second analyte binding agent or a competitive agent positioned distal relative to the terminal buffer flow zone 116.

As has been described above, one of the advantages of the test strips of the present invention is their self-timing property. In order to explain the significance of these properties, a comparison will now be made to the FLEXPACKJHP test strip manufactured by Abbott which is illustrated in FIGS. 6A and 6B.

FIG. 6A illustrates the layout of the test strip. As illustrated, the test strip includes two separate sections 310, 312 which are attached to each other by a hinge 314. Section 310 on the right includes a test strip 316 which includes a sample addition zone 318, a test zone 319, a limit line 320, and a conjugate buffer transfer pad 322. Section 312 on the left includes an absorbent pad 324 which is positioned opposite the sample addition zone 318, a conjugate buffer addition pad 326 which is positioned opposite the conjugate buffer transfer pad 322, and a test window 328 which is positioned opposite the test zone 319. The opposing positionings of the absorbent pad 324, the conjugate buffer addition pad 326, and the test window 328 allows the absorbent pad 324 to contact the sample addition zone 318 and the conjugate buffer addition pad 326 to contact the conjugate buffer transfer pad 322 when the first and second sections 310, 312 are brought into contact with each other. In addition, the test zone 319 can be seen through the test window 328 when the first and second sections 310, 312 are brought together.

FIG. 6B illustrates the operation of the test strip illustrated in FIG. 6A. As illustrated, a conjugate buffer 330 is added to the conjugate buffer addition pad 326. The conjugate buffer addition pad 326 includes a second analyte binding agent (e.g., an antibody) capable of binding to an analyte in the sample to be detected. The second analyte binding agent is labeled with a detectable marker which allows the second analyte binding agent to be visualized. The second analyte binding agent is not specific for the analyte and thus can bind to other components in the sample.

A sample 332 is then taken and added to the sample addition zone 318. Once added, the sample diffuses through the test strip 316 from the sample addition zone 318 across the test zone 319. The test zone 319 includes an immobilized first analyte binding agent (e.g., an antibody) which selectively binds to an analyte in the sample which the test strip is designed to detect. When the sample traverses the test zone 319, analyte in the sample binds to the first analyte binding agent and is immobilized in the test zone 319.

When the diffusion front of the sample reaches the limit line 320, the user is supposed to bring the first and second sections 310, 312 together. Bringing the first and second sections 310, 312 together causes the absorbent pad 326 to draw the sample back toward the sample addition zone 318. Meanwhile, conjugate buffer is transferred to the conjugate buffer transfer pad 322 from the conjugate buffer addition pad 320. The conjugate buffer diffuses from the conjugate buffer transfer pad 322 across the test zone 319. Second analyte binding agent that was stored in the conjugate buffer addition zone 318 diffuses with the conjugate buffer and contacts immobilized analyte in the test zone 319. Observation of the visually detectable marker on the second analyte, binding agent once immobilized in the test zone 319, is used to detect the analyte.

As can be seen from the above description of the operation of the FLEXPACKJHP test strip, it is necessary to determine when the sample reaches the limit line 320 before causing the conjugate buffer to be transferred from the buffer addition zone 318 to the conjugate buffer addition pad 320 and begin flowing toward the test zone 319. It is also necessary to take the affirmative step of contacting the sample addition zone 318 with the absorbent pad 324 in order to cause the sample to be withdrawn from the test zone 319.

The design of the test strips of the present invention, for example those illustrated in FIGS. 2-4, eliminate the need to monitor the test strip to determine when to begin the removal of the sample from the test zone. It is noted that no monitoring is required and that the sample is added after buffer in the test strips of the present invention as opposed to the FLEXPACKJHP test strip.

In addition, since the buffer withdraws automatically, one need not carefully monitor the test strip regarding when to add the sample. Rather, test results using the test strips of the present invention are not dependent on when the sample reaches the test zones after the buffer diffuses from the test zones.

Lateral flow assays according to the invention may find use in a variety of applications. For example, the assays may be used to assay for human diseases, such as infectious diseases, or any other human diseases involving recognizable epitopes (e.g. cancer, autoimmune disease, cardiovascular conditions, hormone testing, and pathology). The assays may also be used in veterinary, food testing, agricultural, or fine chemical applications. The lateral flow assays according to the invention may be performed in variety of ways, including use of a lateral flow assay testing apparatus, such as that disclosed in the application Ser. No. 09/199,255, filed Nov. 23, 1998 which is incorporated herein by reference. In a preferable embodiment, the lateral flow assay testing apparatus comprises a ReLIAJ testing apparatus, available from PraxSys BioSystems (San Ramon, Calif.).

1. Construction of Test Strips According To The Present Invention

Methods and materials for constructing test strips according to the present invention will now be discussed in greater detail. It is noted that the particular construction of the test strip may be varied, depending on the particular assay that the test strip is intended to perform. Variations in the way in which the test strips may be constructed beyond this example are intended to fall within the scope of the invention.

FIG. 7 illustrates a side break-away view of the lateral flow test strip illustrated in FIG. 1. As illustrated in FIG. 7, the test strip 100 may include a backing strip 402 which runs a length of the test strip. A membrane strip 404 is positioned over the backing strip 402 and serves as a diffusion passageway for the test strip. An absorbent pad 408 is positioned over the membrane strip 404 within the absorbent zone 108 which is positioned toward a proximal end of the test strip. A buffer pad 406 is positioned over the membrane strip 404 distal to the absorbent pad 408. An adhesive 409 may be used to attach the buffer pad 406 to the membrane strip 404. One or more test zones 410, 412, 414 may be formed in the membrane strip 404 distal to the sample pad 406. Some of these test zones may be control zones and some may be for measuring an analyte in the sample. A conjugate pad 416 is positioned over the membrane strip 404 distal to the test zones 410, 412, 414 and distal to the terminal buffer flow zone 116. A sample pad is positioned over or distal to the conjugate pad. A protective cover 418 optionally may be positioned over the test zones.

The backing strip may be made of any stable, non-porous material that is sufficiently strong to support the materials and strips coupled to it. Since many assays employ water as a diffusion medium, the backing strip is preferably substantially impervious to water. In a preferred embodiment, the backing strip is made of a polymer film, more preferably a polyvinyl film.

The membrane strip may be made of any substance which has sufficient porosity to allow capillary action of fluid along its surface and through its interior. The membrane strip should have sufficient porosity to allow movement of antibody- or antigen-coated particles. The membrane strip should also be wettable by the fluid used in the sample which contains the analyte to be detected (e.g., hydrophilicity for aqueous fluids, hydrophobicity for organic solvents). Hydrophobicity of a membrane can be altered to render the membrane hydrophilic for use with aqueous fluid, by processes such as those described in U.S. Pat. No. 4,340,482, or U.S. Pat. No. 4,618,533, which describe transformation of a hydrophobic surface into a hydrophilic surface. Examples of substances which can be used to form a membrane strip include: cellulose, nitrocellulose, cellulose acetate, glass fiber, nylon, polyelectrolyte ion exchange membrane, acrylic copolymer/nylon, and polyethersulfone. In a preferred embodiment, the membrane strip is made of nitrocellulose.

The absorbent pad may be formed of an absorbent substance that can absorb the fluid used as the sample and buffer. The absorption capacity of the absorbent pad should be sufficiently large to absorb the fluids that are delivered to the test strip. Examples of substances suitable for use in an absorbent pad include cellulose and glass fiber.

The sample and buffer addition pads may be formed of any absorbent substance. Examples of substances that may be used include cellulose, cellulose nitrate, cellulose acetate, glass fiber, nylon, polyelectrolyte ion exchange membrane, acrylic copolymer/nylon, and polyethersulfone.

As discussed previously, the sample addition pad may serve as the additional role of being the conjugate pad and contain an agent labeled with a detectable marker which is capable of binding to the analyte to be detected in the sample. In competitive assays, the sample addition pad may contain a competitive agent. Alternatively, the test strip may include a conjugate pad separate from the sample addition pad which contains an agent labeled with a detectable marker which is capable of binding to the analyte to be detected in the sample. In competitive assays, the conjugate pad may contain a competitive agent. In FIG. 7, a conjugate pad is shown as element 420 beneath the sample addition pad 416. It is noted that the conjugate pad in FIG. 7 is positioned in the flow path between the sample addition pad 416 and the remainder of the test strip.

The protective cover, if used, may be formed of any material which is impervious to water, and is preferably translucent or transparent. The protective covering may be a single or multiple layers. Preferable materials for use in the protective covering include optically transmissive materials such as polyamide, polyester, polyethylene, acrylic, glass, or similar materials. The protective covering may be clear or not clear depending on method of detection used. In a preferable embodiment, protective covering is optically clear polyester.

2. Assays For Use With Test Strips According To The Present Invention

The test strips of the present invention are intended to be employable with a wide variety of lateral flow assays involving two analyte binding agents which each can bind to an analyte to be detected. At least one of the binding agents should bind selectively to the analyte. More specifically, one of the binding agents should bind to the analyte and not bind to any other components of the sample.

As used herein, the term, "analyte," is intended to refer to any component of a sample (e.g., molecule, compound, or aggregate thereof) which is to be detected and optionally quantitatively determined by an assay test strip. Examples of analytes include proteins, such as hormones and other secreted proteins, enzymes, and cell surface proteins; glycoproteins; peptides; small molecules; polysaccharides; antibodies (including monoclonal or polyclonal Ab and portions thereof); nucleic acids; drugs; toxins; viruses or virus particles; portions of a cell wall; and other compounds possessing epitopes.

The first and second analyte binding agents may be any agents which can bind to the analyte to be detected. A variety of different types of molecules can be used as analyte binding agents, including, for example, antibodies, engineered proteins, peptides, haptens, and lysates containing heterogeneous mixtures of antigens having analyte binding sites. P. Holliger et al., Trends in Biotechnology 13:7-9 (1995); S. M. Chamow et al., Trends in Biotechnology 14:52-60 (1996). If the analyte to be detected is a ligand, a receptor which binds to the ligand can be used, and vice versa. In one particular embodiment, the first and/or second analyte binding agents are antibodies which bind to an immunogenic portion of the analyte.

It is noted that at least one of the first and second analyte binding agents should bind to the analyte and not bind to any of the other components in the sample to be analyzed, referred to herein as an analyte-selective binding agent. In one embodiment, the first analyte binding agent which is immobilized in a test zone is an analyte-selective binding agent and the second analyte binding agent which is labeled with a detectable marker is capable of binding non-selectively to the analyte. In another embodiment, the first analyte binding agent which is immobilized in a test zone is capable of binding non-selectively to the analyte and the second analyte binding agent which is labeled with a detectable marker is an analyte-selective binding agent. In yet another embodiment, both the first and second analyte binding agents are analyte-selective binding agents.

Examples of analyte-selective binding agents include antibodies (monoclonal, polyclonal, and fragments thereof) which have a narrow binding affinity to only a particular type of biomolecule, such as a protein or receptor. The detectable marker attached to the second analyte binding agent may comprise a wide variety of materials, so long as the marker can be detected. Examples of detectable markers include, but are not limited to particles, luminescent labels; colorimetric labels, fluorescent labels; chemical labels; enzymes; radioactive labels; or radio frequency labels; metal colloids; and chemiluminescent labels. Examples of common detection methodologies include, but are not limited to optical methods, such as measuring light scattering, simple reflectance, luminometer or photomultiplier tube; radioactivity (measured with a Geiger counter, etc.); electrical conductivity or dielectric (capacitance); electrochemical detection of released electroactive agents, such as indium, bismuth, gallium or tellurium ions, as described by Hayes et al. (Analytical Chem. 66:1860-1865 (1994)) or ferrocyanide as suggested by Roberts and Durst (Analytical Chem. 67:482-491 (1995)) wherein ferrocyanide encapsulated within a liposome is released by addition of a drop of detergent at the detection zone with subsequent electrochemical detection of the released ferrocyanide. Other conventional methods may also be used, as appropriate.

It may be desired to assay two or more different analytes using the same test strip. In such instances, it may be desirable to employ different detectable markers on the same test strip where each detectable marker detects a different analyte. For example, different detectable markers may be attached to different analyte-selective binding agents. The different detectable markers may be different fluorescent agents which fluoresce at different wavelengths.

When detecting two or more different analytes using the same test strip, separate test zones may optionally be formed on the test strip for each analyte to be detected. The same detectable marker may be used for all of the analytes. Alternatively, different detectable markers, as described above, may be used for the different analytes in order to prevent one test zone being confused with another.

In a preferable embodiment, the detectable marker is a particle. Examples of particles that may be used include, but are not limited to, colloidal gold particles; colloidal sulphur particles; colloidal selenium particles; colloidal barium sulfate particles; colloidal iron sulfate particles; metal iodate particles; silver halide particles; silica particles; colloidal metal (hydrous) oxide particles; colloidal metal sulfide particles; colloidal lead selenide particles; colloidal cadmium selenide particles; colloidal metal phosphate particles; colloidal metal ferrite particles; any of the above-mentioned colloidal particles coated with organic or inorganic layers; protein or peptide molecules; liposomes; or organic polymer latex particles, such as polystyrene latex beads.

A preferred class of particles is colloidal gold particles. Colloidal gold particles may be made by any conventional method, such as the methods outlined in G. Frens, 1973 Nature Physical Science, 241:20 (1973). Alternative methods may be described in U.S. Pat. Nos. 5,578,577, 5,141,850; 4,775,636; 4,853,335; 4,859,612; 5,079,172; 5,202,267; 5,514,602; 5,616,467; 5,681,775.

The selection of particle size may influence such factors as stability of bulk sol reagent and its conjugates, efficiency and completeness of release of particles from conjugate pad, speed and completeness of the reaction. Also, particle surface area may influence steric hindrance between bound moieties. Particle size may also be selected based on the porosity of the membrane strip. The particles are preferably sufficiently small to diffuse along the membrane by capillary action of the conjugate buffer.

Particles may be labeled to facilitate detection. Examples of labels include, but are not limited to, luminescent labels; colorimetric labels, such as dyes; fluorescent labels; or chemical labels, such as electroactive agents (e.g., ferrocyanide); enzymes; radioactive labels; or radio frequency labels.

The number of particles present in the test strip may vary, depending on the size and composition of the particles, the composition of the test strip and membrane strip, and the level of sensitivity of the assay. The number of particles typically ranges between about $1\times10^9$ and about $1\times10^{13}$ particles, although fewer than about $1\times10^9$ particles may be used. In a preferred embodiment, the number of particles is about $1\times10^{11}$ particles.

3. Control Test Zones

As illustrated in FIG. 1, a plurality of test zones 110, 112, 114 may be included on the test strip. Each test zone is located such that an automatic or semi-automatic analytical instrument, or a human reader, may determine certain results of the lateral flow assay.

As discussed previously, immobilized in at least one of the test zones is a first analyte binding agent which is capable of binding to an analyte in the sample which the test strip is designed to detect. In some embodiments, it may be desirable for some of the other test zones to serve as one or more control zones where one or more control binding agents have been immobilized. Control agents capable of binding to the control binding agent may be positioned on the test strip at various locations or added to the test strip when the assay is being performed. The control agents are preferably labeled with a detectable marker, such as the detectable markers described above, to facilitate detection of the control agent binding to the control binding agent immobilized in a control zone.

The control agents and control binding agents may be used in combination to perform a variety of control functions. For example, the control binding pairs may be used to confirm whether the sample and buffer have diff-used properly within the test strip. The control binding pairs are also employable as internal standards and allow analyte measurement results to be compared between different test strips. This can be used to correct for strip-to-strip variability. Such correction would be impractical with external controls that are based, for example, on a statistical sampling of strips. Additionally, lot-to-lot-and run-to-run variations between different test strips may be minimized by the use of control binding pairs. Furthermore, the effects of non-specific binding, as discussed further below, may be reduced. All of these corrections are difficult to accomplish using external, off-strip controls.

A wide variety of agents are known in the art which may be used as a member of the control binding pair. For example, at least one member of the control binding pair may be a naturally occurring or engineered protein. The control binding pair may also be a receptor-ligand pair. Additionally, at least one member of the control binding pair may be an antigen, another organic molecule, or a hapten conjugated to a protein non-specific for the analyte of interest. Descriptions of other suitable members of control binding pairs may be found in U.S. Pat. No. 5,096,837, and include IgG, other immunoglobulins, bovine serum albumin (BSA), other albumins, casein, and globulin.

Desirable characteristics for control agent—control binding agent pairs include, but are not limited to stability in bulk, non-specificity for analyte of interest, reproducibility and predictability of performance in test, molecular size, and avidity of binding for each other.

In a preferred embodiment, members of the control binding pair do not bind to anything that might be present in the test strip, e.g., from the sample. In one embodiment, the control binding agent comprises rabbit anti-dinitrophenol (anti-DNP) antibody and the control agent includes a dinitrophenol conjugated to BSA (bovine serum albumin).

In one preferred embodiment, the second analyte binding agent and the control agent are each separately bound to different particles.

In another preferred embodiment, both the second analyte binding agent which diffuses along the test strip and the control agent are attached to a single species of particle. Attachment may be by non-specific absorption or by traditional conjugate chemistries. Alternatively, a non-covalent binding system, such as biotin-avidin, or even an antibody specific for the second analyte binding agent may be used to attach the analyte binding agent to the particle. Bifunctional and multifunctional reagents may also be used to couple to the second analyte binding agent and the control agent to the particle.

The number of second analyte binding agents and control agents attached to each particle can be varied, depending on what is appropriate for a particular assay. For example, two copies of the second analyte binding agent and one copy of the control agent may be attached to each particle. Alternatively, one copy of the second analyte binding agent and two copies of the control agent may be attached to each particle. Other variations on the ratios between second analyte binding agent: control agent: particle can be used depending on the particular assay in which they are to be employed, these variations being intended to fall within the scope of the present invention.

When the test strip includes more than one control zone, the control zones may be used to create a calibration curve against which a wide variety of analyte measurement results may be compared. The control zones may also be used to troubleshoot whether the test strip operated appropriately.

In one embodiment, the test strip has at least two control zones that have about the same concentration of control binding agent. It is noted that it is typically easier and more economical to deliver the same amount of control binding agent to different control zones.

Alternatively, the concentration of control agent in one of the control zones may be greater than the concentration of control agent in another of the control zones. In this instance, the amount of control binding pairs will be higher in the control zone with the higher concentration of control binding agent than in the other control zone.

Incorporating more than one control zone on a test strip can be used to provide the test strip with a wider dynamic range than conventional lateral flow assays. In preferred embodiments, test strips with 2, 3 or more control zones are used with a relative scale methodology that permits mapping of amounts of control binding pairs detected onto the same scale on which amounts of analyte detected are reported.

Incorporating more than one control zone on a test strip can also be used to evaluate the performance of the test strip. For example, an apparatus for evaluating an analyte in a sample can determine a ratio between the measured amounts of control binding agent in at least two control measurement zones, and detect whether an error has occurred in a test strip based on whether the determined ratio falls outside of predetermined acceptable maximum and minimum ratio ranges for that test strip. If an error is not deemed to have occurred, the apparatus may proceed to evaluate the amount of analyte in the sample. If an error is deemed to possibly have occurred, the instrument may notify an instrument operator of the potential error.

When the concentrations of control binding agent in the first and second control zones are about the same, the predetermined acceptable maximum and minimum ratio may both be near about 1. When the concentrations of control binding agent in the first and second control zones are different (e.g., the first control zone has three times as much control binding agent as the second control zone), the predetermined acceptable maximum and minimum ratio may both be near about 3.

An apparatus used to measure the test strips may include executable logic that determines whether the concentrations of control binding agent in the first and second control zones are within a predetermined acceptable maximum and minimum ratio.

An apparatus used to measure the test strips may also include executable logic that evaluates the amount of analyte in the sample based on a combination of the measured amount of first analyte bound in the analyte measurement zone and the measured amount of control binding agent bound in the first control measurement zone.

The apparatus may include executable logic that evaluates the amount of analyte in the sample based on a combination of the measured amount of first analyte bound in the analyte measurement zone and the measured amount of control binding agent bound in the first and second control measurement zones.

The amount of control binding pairs in a given control zone may be mapped onto the same measurement scale on which the amount of analyte is reported, a calibration curve may be drawn through the values of the binding pairs in the high and low control zones.

When more than two control zones are present, a curve may be generated that reflects any nonlinearities present in the assay between the amount of analyte detected and the measurement against which the amount might be mapped. While such nonlinearities might otherwise affect assays that assume a relatively linear relationship, they can be corrected for using multiple control zones. 2, 3 or more control zones may be used.

In another embodiment, a single control zone may comprise more than one type of control agent. This may be of use in embodiments where there are more than one population of analyte binding agents and analyte non-specific agents coupled to a detection agent. For example, when it is desired to assay two or more analytes of interest on the same assay strip, two populations of analyte binding agents and analyte non-specific agents coupled to a detection agent may be prepared. Different detection agents may be used for each population, allowing a distinction to be drawn between results for the two different analytes of interest. In such circumstances, it may be desirable to use control zones comprising different control agents or control binding pairs.

The control zones may be located in a variety of locations within the group of test zones. It is noted that the test zones may be placed on various locations on the test strip, depending on the flow design of the test strip consistent with the present invention. In a preferred embodiment, the control zones are adjacent the test zones used to detect analytes in the sample. In a particularly preferred embodiment, at least one control zone is positioned proximal to a test zone used to detect an analyte in a sample and at least one control zone is positioned distal to that test zone.

By positioning the analyte test zone between two control zones, the control zones can be effectively used to confirm several operations of the test strip. For example, the control zones can confirm that buffer was added and that sufficient buffer was added so that the buffer completely traversed the analyte test zone in both directions. Development of the analyte test zone confirms that the sample was added. By measuring a relationship between the control zones, it is also possible to confirm that sufficient sample was added and that the strip flowed properly.

Assays are performed using a test strip which includes one or more control regions as part of the test regions in the same manner as described in regard to FIGS. 2A-2H and 3A-3H. It is noted that either the test strip or the buffer may include the control agent which binds to the control binding agent immobilized, for example, in test zones 110 and 114 of FIGS. 2A-2H and test zones 210 and 214 of FIGS. 3A-3H. When the buffer is added, the control agent diffuses with the buffer and binds to the control binding agent immobilized in the control zones. When the sample is added, the sample serves to wash any unbound control agent away from the control zone.

Amounts of control agents immobilized in the control zones are detected along with the detection of amounts of second analyte binding agent immobilized in the test zones. As noted above, it is preferred for the control agents and the second analyte binding agent to be labeled with a detectable marker which facilitates their detection. The amount of detectable marker in each test zone can be readily determined by a variety of techniques known in the art, depending on the type of detectable markers being employed. Common examples of detection techniques include optical methods (light scattering, simple reflectance, luminometer or photomultiplier tube); radioactivity; electrical conductivity; dielectric capacitance; electrochemical detection of released electroactive agents; as has been noted above.

Once the amount of detectable markers has been measured in each test zone, these measurements may be used to detect and preferably quantify the amount of analyte present, preferably by also calibrating the test strip using the amounts of detectable markers in the control zones. For example, when one or more control zones are employed, the amount of control agent immobilized in one or more of the control zones may be used to quantify the amount of first analyte binding agent relative to one or more of the control zones. These relative intensity measurements may then be used to more accurately determine the number of copies of analyte present in the measurement volume.

One feature of using multiple control zones is the ability to create a relative scale for analyte measurements. Once the amounts of detectable markers have been quantified, these amounts may then be mapped onto another measurement scale. For example, while the results from measuring the analyte may be measured based on an absolute measurement of the analyte, the results reported may be more meaningful in other units, such as an intensity relative to that of a control zone or control zones, referred to herein as Relative Intensity or RI. Results may also be expressed as the number of copies of analyte present in the measurement volume. The mapping of the amount of analyte detected onto other measurement scales is a preferable embodiment for reporting results of the inventive assay.

In addition to reporting the assay results on a continuous scale, either directly as the amount of analyte detected or indirectly as a measurement scale onto which the amount of analyte detected has been mapped, the inventive assays may be used in a "cut-off" style assay. If the detectable marker is detected in an analyte binding zone, the amount of detectable marker detected may be compared against a cut-off value. A cut-off value is the value above which the test may be considered positive; that is, the analyte of interest is present in the fluid sample to some degree of statistical confidence. Below the cut-off value, the test is generally considered not positive—either the analyte of interest is not present or the inventive lateral flow assay did not detect its presence. While a cut-off may established based upon a directly measured value, such as the amount of analyte detected, the results may be more meaningful if reported on an indirect, or relative, scale.

A cut-off lateral flow assay is more desirable as the measurement separation between a negative value and a positive value increases. A negative value is the reported value on the continuous scale in the case where the analyte of interest is statistically not present. Conversely, a positive value is the reported value on the continuous scale in the case where the analyte of interest is statistically present. As these values converge, the likelihood reduces of being able to statistically tell positives and negatives apart.

Also desirable is a cut-off lateral flow with increased precision at the cut-off. When there is less variation at the chosen cut-off, it is more likely that a positive can be accurately considered a positive and a negative be accurately considered a negative.

Assay results may be mapped onto either a "relative," discussed above, or an "absolute" scale. Absolute scales are measured in actual physical units, such as number of copies of analyte per milliliter of fluid. Measurement in the absolute scale may be preferable in testing for certain diseases or conditions, such as tests for cancer markers, such as for PSA or hormones such as TSH. In such preferable embodiments, the result may be expressed in units, such as ng/ml. Accordingly, the control zones may have value assigned concentrations of control agent. In an extension of the relative measurement concept, the density of reflectance (DR) values of a series of standards of known analyte concentration may be measured and the intensities relative to the controls (RI values) calculated as previously described. The RI values may then be plotted against analyte concentration to construct a standard curve in which the RI values are assigned concentration values of the analyte of interest. The RI of a sample may then be read on this value assigned standard curve, yielding a result labeled in the desired units.

Many circumstances may affect the absolute reactivity of lateral flow assays, including, but not limited to, reagent flow variations, manufacturing-derived variations, operator induced variations, environmentally induced variations and sample effects. With conventional lateral flow assays, any of these variations may act to repress or arguably enhance reactivity of one strip over another, resulting in possible false negative or false positive results. Not controlling for these or other variations may result in significant imprecision, non-reproducibility, lack of sensitivity and lack of specificity of the tests.

Lateral flow assays are also subject to a number of interferences which might affect the absolute amount of binding of either analyte binding agent or control agent to the test zones. Influencing factors may include: 1) variability in the release of the first analyte binding agent or the control agent from a conjugate pad, 2) device to device variation in the non-specific binding of the analyte binding population to the test strip, 3) variability in the movement of the analyte binding population through or along the test strip during the assay due to variations in reagent flow rates between when a portion of the strip is dry and when a portion of the strip is wet, variations in the pore size of the test strip or membrane strip materials or non-specific aggregation of the analyte binding agent. Variability of absolute measurements of binding due to these or other factors may therefore be unacceptably high in conventional lateral flow assays.

The use of control zones on test strips is also described in greater detail in application Ser. No. 09/198,118, filed Nov. 23, 1998 and application Ser. No. 09/638,668, filed Aug. 14, 2000, which are each incorporated herein by reference.

EXAMPLES

1. Construction of Test Strip

In this example, the construction of a test strip having a design as illustrated in FIGS. 1 and 7 is described. Backed sheets of nitrocellulose, for example, Millipore STHF or HF 90 nitrocellulose (4.8 cm×20 cm) were coated by longitudinally dispensing one antigen test band and two control bands onto the nitrocellulose using a Biodot Quanti-3000 XYZ Dispensing Platform with Biojets operating at a frequency of 180 Hz., 20.83 nl/drop and 0.75 µl/cm. The nitrocellulose sheets were then dried for one hour at 37° C. in a forced air incubator. Coated nitrocellulose sheets were stored desiccated at room temperature in foil pouches.

Gelman 8980 glass fiber pads, for use as conjugate pads, were preblocked by dipping in a solution of PBS containing 10 mg/ml BSA, 1% (w/v) Triton X-100, 2.5% (w/v) sucrose, 0.3% (w/v) polyvinyl pyrrolidone K-30 and 2 mg/ml rabbit IgG. The preblocked pads were then dried for two hours in a forced air incubator. A solution of control and test conjugates in PBS containing 10 mg/ml BSA, 1% (w/v) Triton X-100, 2.5% (w/v) sucrose, 0.3% (w/v) polyvinyl pyrrolidone K-30 and 2 mg/ml rabbit IgG was longitudinally dispensed on the preblocked pads using a Biodot Quanti-3000 XYZ Dispensing Platform with Biojets operating at a frequency of 120 Hz., 104.17 nl/drop and 2.5 µl/cm. The conjugate pads were coated with conjugate in patterns of from one to four lines per cm with one pattern coated on each 1.3 cm×20 cm pad. Coated conjugate pads were vacuum dried at 2 Torr for two hours at room temperature.

Cytosep 1662 sheets, for use in preparing sample pads, were preblocked by dipping in a solution of PBS 10 mg/ml BSA, 1% (w/v) Triton X-100, 2.5% (w/v) sucrose and 0.3% polyvinyl pyrrolidone K-30. The sheets were then dried for two hours in a forced air incubator. After drying sheets were slit to strips 7.5 mm wide using a G&L Precision Die Cutting Drum Slitter.

Cytosep 1662 sheets, for use in preparing conjugate buffer pads, were preblocked by dipping in a solution of PBS 10 mg/ml BSA, 1% (w/v) Triton X-100, 2.5% (w/v) sucrose, 0.3% polyvinyl pyrrolidone K-30, 2 mg/ml Rabbit IgG, 1 mg/ml Goat IgG and 0.33 mg/ml heterophyllic blocking reagent 1 (HBR-1) then drying for two hours in a Forced air incubator. The sheets were then slit to strips 0.75 cm wide using a G&L Precision Die Cutting Drum Slitter and further cut to 0.75 cm×1.2 cm pads using a Biodot Guillotine cutter.

Test strips were prepared by affixing one 4.8 cm×20 cm backed nitrocellulose sheet, and one 1.3 cm×20 cm coated preblocked conjugate pad onto one adhesive coated 0.010" thick 6 cm×20 cm vinyl backing sheet (G&L Precision Die Cutting). One 0.75 cm×20 cm sample pad was then affixed to the nitrocellulose using double sided adhesive. Strips 0.5 cm wide were cut from the assembled sheet with a Kinematics Automation Matrix 2360 Guillotine Cutter. To assemble the test strip into a test cartridge, illustrated in FIGS. 5A and 5B, the strip was placed in the bottom half of the holder and a 0.6 cm×2.7 cm absorbent pad was placed over the top of the strip. A 0.75 cm×1.2 cm preblocked conjugate buffer pad was then placed over the conjugate pad and aligned with the bottom of the strip and the pins of the top half of the holder aligned with the holes of the bottom half and the holder tightly pressed together.

2. Thyroid Stimulating Hormone (TSH) Assay

Strips used in this example were coated with 3 mg/ml rabbit anti-dinitrophenyl (anti-DNP) in the high control band and 0.8 mg/ml rabbit anti-dinitrophenyl in the low control band and 4 mg/ml affinity goat anti-TSH in the antigen band on Millipore SRHF nitrocellulose. The order of the bands on the strip was low control zone closest to the sample addition pad, high control zone farthest from the sample addition pad (closest to the buffer addition pad) and antigen band (anti-TSH) between the low control zone and the high control zone. Nitrocellulose sheets were coated and strips prepared as in Example 1.

Preblocked conjugate pads were coated with a mixture of 0.2 volumes of Anfi-DNP-32 nm gold conjugate (OD 520 nm approximately 83) and 0.13 volumes of monoclonal anti-TSH 32-nm gold conjugate (OD 520 nm approximately 102) in a total of four volumes of PBS containing 10 mg/ml BSA, 1% (w/v) Triton X-100, 2.5% sucrose and 0.3% (w/v) polyvinyl pyrrolidone K-30. The mixture was dispensed onto preblocked conjugate pads as described in Example 1.

The assay was carried out by placing the cassette on the lab bench and then adding 40 µl of release buffer (5.5×PBS, 10 mg/ml BSA, 0.025% casein, 0.325% Tween 20, 2 mM EDTA, 0.1% sodium azide) containing 160 µg/ml BSA-DNP to the sample addition port of the cassette. The cassette was immediately placed in a ReLIA™ machine set up to run and read the ReLIA™ assay for the detection of TSH. At the prompts, sample number and assay time were entered, triggering the sample addition clock. After a time sufficient for prewetting of the strip to a point distal to the low control zone (56 seconds, machine time constant of 40), the machine prompted the user to add 150 μl of the samples shown in FIG. 8 to the conjugate buffer port of the cassette. Strip temperature was set to 30° C. and the strips were read after 20 minutes. Relative intensity values of the samples were generated by calculating the ratio of the density of reflectance of the antigen band to the density of reflectance of the high control band.

Table 1 below provides a definition for the various figure headings describing the test results shown in FIG. 8 as well as in FIG. 10.

TABLE 1

| | |
|---|---|
| HC(Dr) | Raw density of reflectance value for the high control band |
| LC (Dr) | Raw density of reflectance value for the low control band |
| HC/LC | Ratio of the high control band to the low control band. (this ratio is used as a quality control check for each individual strip run) |
| Specimen/ HC | Ratio is the actual value used by the software to generate the result. Using this RI ratio helps to normalize strip to strip variability. |
| μIU/mL | Micro international units per milliliter - the quantitative level of PSH in the sample calculated from the assay standard curve |

Figure 9:
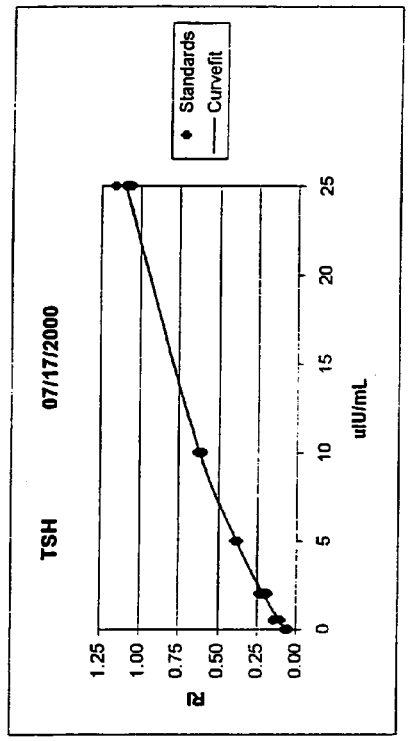
FIG. 9 shows a standard curve derived from the TSH assay results shown in FIG. 8.

As shown in FIG. 9, a standard curve was calculated from the data summarized therein relating the RI value given by a TSH standard to the TSH concentration of the standard. This standard curve was then used to determine the mean TSH concentration of an unknown sample, the standard deviation on the mean and percent CV, using sixteen strips, each from a different coated nitrocellulose sheet, from a single lot of the ReLIA™ TSH assay. As shown in FIG. 9, the percent coefficient of variation on the mean TSH concentration of 8.87 micro International units per milliliter, determined by the ReLIA™ TSH assay, was 5.2% demonstrating the high reproducibility of the RELIA™ TSH assay.

3. Prostate Specific Antigen (PSA) Assay

Strips used in this example were coated with 3 mg/ml rabbit anti-dinitrophenyl (anti-DNP) in the high control band and 1.0 mg/ml rabbit anti-dinitrophenyl in the low control band and 4 mg/ml affinity goat anti-PSA in the antigen band on Millipore HF 135 nitrocellulose. The order of the bands on the strip was low control zone closest to the sample addition pad, high control zone farthest from the sample addition pad (closest to the buffer addition pad) and antigen band (anti-PSA) between the low control zone and the high control zone. Nitrocellulose sheets were coated and strips prepared as in Example 1.

Preblocked conjugate pads were coated with a mixture of 0.2 volumes of Anti-DNP-32 nm gold conjugate (OD 520 nm approximately 83) and 0.14 volumes of monoclonal anti-PSA 32-nm gold conjugate (OD 520 nm approximately 106) in a total of four volumes of PBS containing 10 mg/ml BSA, 1% (w/v) Triton X-100, 2.5% sucrose and 0.3% (w/v) polyvinyl pyrrolidone K-30. The mixture was dispensed onto preblocked conjugate pads as described in Example 1.

The assay was carried out by placing the cassette on the lab bench and then adding 40 μl of release buffer (5.5×PBS, 10 mg/ml BSA, 0.025% casein, 0.325% Tween 20, 2 mM EDTA, 0.1% sodium azide) containing 160 μg/ml BSA-DNP to the sample addition port of the cassette. The cassette was immediately placed in a ReLIA™ machine set up to run and read the ReLIA™ assay for the detection of PSA. At the prompts, sample number and assay time were entered, triggering the sample addition clock. After a time sufficient for prewetting of the strip to a point distal to the low control zone (56 seconds, machine time constant of 40), the machine prompted the user to add 150 μl of the samples shown in FIG. 10 to the conjugate buffer port of the cassette. Strip temperature was set to 30° C. and the strips were read after 15 minutes. Relative intensity values of the samples were generated by calculating the ratio of the density of reflectance of the antigen band to the density of reflectance of the high control band.

Figure 11:
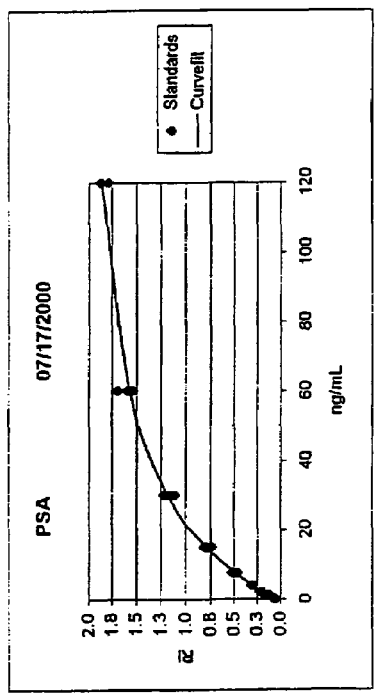
FIG. 11 shows a standard curve derived from the PSA assay results shown in FIG. 10.

As shown in FIG. 11, a standard curve was calculated from the data summarized therein relating the RI value given by a PSA standard to the PSA concentration of the standard. This standard curve was then used to determine the mean PSA concentration of an unknown sample, the standard deviation on the mean and the percent CV, using sixteen strips, each from a different coated nitrocellulose sheet, from a single lot of the ReLIA™ PSA assay. As shown in FIG. 11, the percent coefficient of variation on the mean PSA concentration of 9.00 nanograms per milliliter, determined by the ReLIA™ PSA assay, was 8.9% demonstrating the high reproducibility of the ReLIA™ PSA assay.

4. ReLIA TSH (Thyroid Stimulating Hormone) Stop Flow Assay, Sample Added at Top and Bottom In this example, the construction of the test strip used was as follows. In general, the test strip used has a design as illustrated in FIGS. 1 and 7. Backed sheets of nitrocellulose, for example, Millipore STHF or HF 90 nitrocellulose (4.8 cm×20 cm) were coated by longitudinally dispensing one antigen test band and two control bands onto the nitrocellulose using a Biodot Quanti-3000 XYZ Dispensing Platform with Biojets operating at a frequency of 180 Hz., 20.83 nl/drop and 0.75 μl/cm. The nitrocellulose sheets were then dried overnight at 37° C. in a forced air incubator. Coated nitrocellulose sheets were stored desiccated at room temperature in foil pouches.

Gelman 8980 glass fiber pads, for use as conjugate pads, were preblocked by dipping in a solution of 10 mM Sodium Borate pH 9.0 containing 0.1% polyethylene glycol (MW 20000) and 5% Trehalose. The preblocked pads were then dried for two hours in a forced air incubator. A solution of control and test conjugates, in 10 mM Sodium Borate pH 9.0 containing 0.1% polyethylene glycol (MW 20000) and 5% Trehalose, was longitudinally dispensed on the preblocked conjugate pads using a Biodot Quanti-3000 XYZ Dispensing Platform with Biojets operating at a frequency of 120 Hz., 104.17 nl/drop and 2.5 μl/cm. The conjugate pads were coated with conjugate in patterns of from one to four lines per cm with one pattern coated on each 1.3 cm×20 cm pad. Coated conjugate pads were vacuum dried at 2 Torr for two and one half hours at room temperature.

Cytosep 1662 sheets, for use in preparing sample pads, were preblocked by dipping in a solution of PBS 10 mg/ml BSA, 1% (w/v) Triton X-100, 2.5% (w/v) sucrose and 0.3% polyvinyl pyrrolidone K-30. The sheets were then dried for two hours in a forced air incubator. After drying sheets were slit to strips 7.5 mm wide using a G&L Precision Die Cutting Drum Slitter.

Cytosep 1662 sheets, for use in preparing conjugate buffer pads, were preblocked by dipping in a solution of PBS 10 mg/ml BSA, 1% (w/v) Triton X-100, 2.5% (w/v) sucrose, 0.3% polyvinyl pyrrolidone K-30, 2 mg/ml Rabbit IgG, 1 mg/ml Goat IgG and 0.33 mg/ml heterophyllic blocking reagent 1 (HBR-1) then drying for two hours in a Forced air incubator. The sheets were then slit to strips 0.5 cm wide using a G&L Precision Die Cutting Drum Slitter and further cut to 0.5 cm×1.2 cm pads using a Biodot Guillotine cutter.

Test strips were prepared by affixing one 4.8 cm×20 cm backed nitrocellulose sheet, and one 1.3 cm×20 cm coated preblocked conjugate pad onto one adhesive coated 0.010" thick 6 cm×20 cm vinyl backing sheet (G&L Precision Die Cutting). One 0.75 cm×20 cm sample pad was then affixed to the nitrocellulose using double sided adhesive. Strips 0.5 cm wide were cut from the assembled sheet with a Kinematics Automation Matrix 2360 Guillotine Cutter. To assemble the test strip into a test cartridge, illustrated in FIGS. 5A and 5B, the strip was placed in the bottom half of the holder and a 0.6 cm×2.7 cm absorbent pad was placed over the top of the strip. A 0.5 cm×1.2 cm preblocked conjugate buffer pad was then placed over the conjugate pad and aligned with the bottom of the strip and the pins of the top half of the holder aligned with the holes of the bottom half and the holder tightly pressed together.

Strips used in this example were coated with 500 μg/ml Dinitrophenyl Bovine Serum Albumin (BSA-DNP) in the high control band, 100 μg/ml BSA-DNP in the low control band and a 4 mg/ml Affinity Goat anti-TSH in the antigen band. The order of the bands on the strip was low control zone closest to the conjugate pad, antigen band between the low control zone and the high control zone and the high control zone farthest from the conjugate pad and closest to the absorbent pad. Nitrocellulose sheets were coated and strips prepared as described above.

Conjugate pads preblocked with 2 mM Sodium Borate pH 9.0 containing 5% Trehalose were coated with a mixture of Anti-DNP conjugate [Rabbit anti-DNP (2×)] –30 nm gold and anti-TSH conjugate [Monoclonal anti-TSH (2×)]–30 nm gold. This was accomplished by mixing 0.3 volumes of the anti-DNP stock conjugate solution (OD 520 approximately 100) and 0.7 volumes of the anti-TSH conjugate (OD 520 approximately 124) with two volumes 2 mM Sodium Borate pH 9.0 containing 5% Trehalose and one volume 2 mM Sodium Borate pH 9.0. The mixture was dispensed onto preblocked conjugate pads as described above.

The assay was carried out by placing the cassette on the lab bench and then adding 50 μl of the sample to the sample pad through the proximal port of the sample cassette. The cassette containing the strip was placed in a ReLIA™ machine set up to run and read the ReLIA™ assay for the detection of TSH. At the prompt additional 100 μl of the sample was added to the distal sample port of the cassette. Assay temperature was set at 30° C. and the strips were read after 20 minutes. Relative intensity (RI) values of the samples were calculated by dividing the density of reflectance of the sample (test) band by the density of reflectance of the high control band. A standard curve for the TSH assay was calculated from RI values of TSH standards and programmed into the ReLIA™ machine using a 4 parameter logistic curve fit.

As shown in FIG. 12, the performance of the ReLIA™ TSH assay when sample was added to both the top and bottom ports was compared to that when sample was added only to the bottom port. The data demonstrate that the precision on the high control density of reflectance was higher when sample was added to the top and bottom ports versus the bottom port alone. This translated into precision on the measured level of TSH which was at least equivalent to that obtained when sample was added to the bottom port alone and, in most cases, better.

Figures 13, 14:
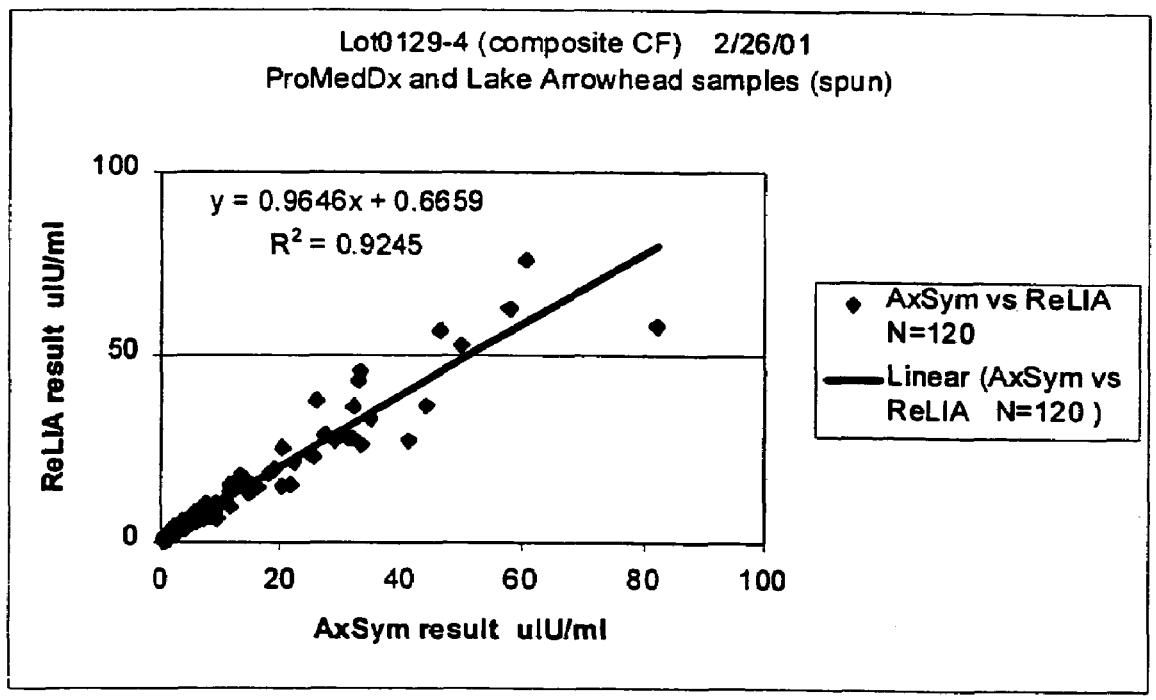
FIG. 13 illustrates the reproducible of measuring TSH levels using the test strip of example 4.
FIG. 14 illustrate TSH values relative to a standard curve for the test strip of example 4.

In FIG. 13 the performance of the ReLIA™ TSH assay using quality control samples representing normal (approximately 1 μIU/mL), borderline elevated (approximately 5 μIU/mL) and elevated (approximately 25 μIU/mL) levels of TSH is displayed. The assay was highly reproducible at all three TSH levels with CV values under 9%.

As shown in FIG. 14, when the assay protocol employing sample addition from both the upper and lower ports was used, ReLIA™ values for TSH in patient samples, calculated by the machine from the standard curve, correlated well with TSH levels measured by the reference method.

It will be apparent to those skilled in the art that various modifications and variations can be made in the apparatus and methods of the present invention without departing from the spirit or scope of the invention. Thus, it is intended that the present invention cover the modifications and variations of this invention provided they come within the scope of the appended claims and their equivalents. Additionally, the following examples are appended for the purpose of illustrating the claimed invention, and should not be construed so as to limit the scope of the claimed invention.

What is claimed is:

1. A test strip adapted to receive a sample and detect an analyte therein, the test strip comprising:
    a buffer addition zone to which a buffer may be added;
    an absorbent zone positioned in a first flow direction relative to the buffer addition zone;
    one or more test zones positioned in a second, different, flow direction relative to the buffer addition zone, at least one of the test zones including a first analyte binding agent immobilized therein which is capable of binding to the analyte to be detected;
    a terminal buffer flow zone positioned in the second flow direction relative to the one or more test zones,
    the absorbent zone having an absorption capacity relative to the other zones of the test strip such that when a volume of buffer within a predetermined buffer volume range for the test strip is added to the buffer addition zone, the buffer initially diffuses from the buffer addition zone both in the first flow direction to the absorbent zone and in the second flow direction past the one or more test zones to a diffusion point within the terminal buffer flow zone and then reverses flow, and diffuses in the first flow direction past the one or more test zones toward the absorbent zone;
    and a sample addition zone positioned in the second flow direction relative to where the buffer reverses flow, to which a sample may be added.

2. The test strip according to claim 1 wherein the test strip further includes a zone positioned on the test strip in the second flow direction relative to where the buffer reverses flow, which includes a second analyte binding agent which is capable of binding to the analyte and diffusing to the one or more test zones.

3. The test strip according to claim 2 wherein the second analyte binding agent is capable of binding to components in the sample other than the analyte.

4. The test strip according to claim 2 wherein the second analyte binding agent does not bind to components in the sample other than the analyte.

5. The test strip according to claim 2 wherein the second analyte binding agent is labeled with a detectable marker.

6. The strip according to claim 2 wherein the second analyte binding agent is attached to a particle which is capable of diffusing to the one or more test zones.

7. The test strip according to claim 2 wherein the zone containing the second analyte binding agent is positioned on the test strip in the first flow direction relative to the sample addition zone.

8. The test strip according to claim 2 wherein the zone containing the second analyte binding agent is the sample addition zone.

9. The test strip according to claim 1 wherein the test strip further includes a zone positioned on the test strip in the second flow direction relative to where the buffer reverses flow, which includes a competitive agent which is capable of competing with the analyte to bind to the first analyte binding agent.

10. The test strip according to claim 9 wherein the competitive agent binds to the first analyte binding agent and does not bind to components in the sample other than the first analyte binding agent.

11. The test strip according to 9 wherein the competitive agent is labeled with a detectable marker.

12. The test strip according to claim 9 wherein the competitive agent is attached to a particle which is capable of diffusing to the one or more test zones.

13. The test strip according to claim 9 wherein the zone containing the competitive agent is positioned on the test strip in the first flow direction relative to the sample addition zone.

14. The test strip according to claim 9 wherein the zone containing the competitive agent is the sample addition zone.

15. The test strip according to claim 1 wherein the sample addition zone is positioned relative to the test zones such that sample added to the sample addition zone at the same time as buffer is added to the buffer addition zone reaches the distal diffusion point after the buffer has diffused to the diffusion point and reversed flow.

16. The test strip according to claim 1 wherein the sample addition zone is positioned relative to the test zones such that sample added to the sample addition zone at the same time as buffer is added to the buffer addition zone reaches the test zones after the buffer has diffused in the second flow direction past the test zones.

17. The test strip according to claim 1 wherein the predetermined buffer volume range is between about 10 and 250 µL.

18. The test strip according to claim 1 wherein the predetermined buffer volume range is between about 20 and 200 µL.

19. The test strip according to claim 1 wherein the predetermined buffer volume range is between about 20 and 100 µL.

20. The test strip according to claim 1 wherein the predetermined buffer volume range is between about 40 and 60 µL.

21. The test strip according to claim 1 wherein the terminal buffer flow zone has a length of between about 3 and 10 mm.

22. The test strip according to claim 1 wherein the first analyte binding agent does not bind to components in the sample other than the analyte.

23. The test strip according to claim 1 wherein the first analyte binding agent is selected from the group consisting of antibodies, engineered proteins, peptides, haptens, lysates containing heterogeneous mixtures of antigens having analyte binding sites, ligands and receptors.

24. The test strip according to claim 1 wherein the test zones further include at least a first control zone with a control binding agent immobilized therein.

25. The test strip according to claim 1 wherein the test zones further include a first control zone with a control binding agent immobilized therein, and a second control zone with a same control binding agent immobilized therein as the first control zone, the first and second control zones containing a different amount of the control binding agent immobilized therein.

26. The test strip according to claim 1 wherein the test zones further include a first control zone with a control binding agent immobilized therein, and a second control zone with a same control binding agent immobilized therein as the first control zone, the first and second control zones containing about the same amount of the control binding agent immobilized therein.

27. The test strip according to claim 1 wherein the test zones further include first and second control zones each with a control binding agent immobilized therein, the first and second control zones positioned adjacent to, and on each side of, the test zone including the first analyte binding agent.

28. The test strip of claim 1, wherein the test strip comprises a buffer pad in the buffer addition zone and a double-sided adhesive between the buffer pad and the test strip.

29. A test strip adapted to receive a sample and detect an analyte therein, the test strip comprising:
a buffer addition zone to which a buffer may be added;
an absorbent zone positioned in a first flow direction relative to the buffer addition zone;
one or more test zones positioned in a second, different, flow direction relative to the buffer addition zone, at least one of the test zones including a first analyte binding agent immobilized therein which is capable of binding to the analyte to be detected;
a terminal buffer flow zone positioned in the second flow directed relative to the one or more test zones,
the absorbent zone having an absorption capacity relative to the other zones of the test strip such that when a volume of buffer within a predetermined buffer volume range for the test strip is added to the buffer addition zone, the buffer diffuses to a diffusion point within the terminal buffer flow zone and then reverses flow independent of user intervention, and flow back in the first flow direction past the one or more test zones toward the absorbent zone;
and a sample addition zone positioned in the second flow direction relative to where the buffer reverses flow, to which a sample may be added.

30. A test strip adapted to receive a sample and detect an analyte therein, the test strip comprising:
a buffer addition zone to which a buffer may be added;
an absorbent zone positioned in a first flow direction relative to the buffer addition zone;
one or more test zones positioned in a second, different, flow direction relative to the buffer addition zone, at least one of the test zones including a first analyte binding agent immobilized therein which is capable of binding to the analyte to be detected;
a terminal buffer flow zone positioned in the second flow direction relative to the one or more test zone,
the absorbent zone having an absorption capacity relative to the other zones of the test strip such that when a volume of buffer within a predetermined buffer volume range for the test strip is added to the buffer addition zone, the buffer diffuses to a diffusion point within the terminal buffer flow zone and then reverses flow and flows back in the first flow direction past the one or more test zones toward the absorbent zone;
and a sample addition zone positioned in the second flow direction relative to where the buffer reverses flow, to which a sample may be added,
wherein reversal of flow of the buffer within the terminal buffer flow zone is controlled by the predetermined amount of buffer added to the test.

* * * * *